US010286198B2

(12) United States Patent
Dang et al.

(10) Patent No.: US 10,286,198 B2
(45) Date of Patent: May 14, 2019

(54) MICROCHIP MEDICAL SUBSTANCE DELIVERY DEVICES

(71) Applicant: International Business Machines Corporation, Armonk, NY (US)

(72) Inventors: Bing Dang, Chappaqua, NY (US); Duixian Liu, Scarsdale, NY (US); Jean-Olivier Plouchart, New York, NY (US)

(73) Assignee: International Business Machines Corporation, Armonk, NY (US)

( * ) Notice: Subject to any disclaimer, the term of this patent is extended or adjusted under 35 U.S.C. 154(b) by 411 days.

(21) Appl. No.: 15/094,003

(22) Filed: Apr. 8, 2016

(65) Prior Publication Data
US 2017/0291019 A1    Oct. 12, 2017

(51) Int. Cl.
*A61K 9/22*    (2006.01)
*A61M 31/00*    (2006.01)
*A61K 9/00*    (2006.01)

(52) U.S. Cl.
CPC .......... *A61M 31/002* (2013.01); *A61K 9/0009* (2013.01); *A61K 9/0097* (2013.01);
(Continued)

(58) Field of Classification Search
CPC ........ A61K 9/0097; A61M 2205/0244; A61M 31/002; A61N 1/0428; A61N 1/0444; A61N 1/0448
See application file for complete search history.

(56) References Cited

U.S. PATENT DOCUMENTS 6,969,382 B2    11/2005 Richter
7,455,667 B2    11/2008 Uhland et al.
(Continued)

FOREIGN PATENT DOCUMENTS

CN    201725352 U    1/2011
CN    202600746 U    12/2012
(Continued)

OTHER PUBLICATIONS

E.E. Nuxoll et al., "BioMEMS Devices for Drug Delivery," IEEE Engineering in Medicine and Biology Magazine, Jan./Feb. 2009, pp. 31-39.
(Continued)

*Primary Examiner* — Rebecca E Eisenberg
(74) *Attorney, Agent, or Firm* — Daniel P. Morris; Ryan, Mason & Lewis, LLP

(57) ABSTRACT

Devices and methods are provided for controlled delivery of medical substances such as drugs and medication. For example, a microchip medical substance delivery device includes a control system, and a medical substance capsule that comprises a medical substance contained with a reservoir, and a release structure to release the medical substance from within the reservoir in response to an activation signal generated by the control system. The control system comprises a wireless signal receiving element, processor, actuator circuit, and power supply source. The wireless signal receiving element captures a wireless signal. The processor detects an activation code embedded within the captured wireless signal, and generates an actuator control signal in response to the detection of the activation code. The actuator circuit generates the activation signal in response to the actuator control signal generated by the processor. The power supply source provides power to operate components of the control system.

20 Claims, 15 Drawing Sheets

(52) U.S. Cl.
CPC ............... *A61M 2205/3523* (2013.01); *A61M 2205/3569* (2013.01); *A61M 2205/3592* (2013.01)

(56) References Cited

U.S. PATENT DOCUMENTS

| | | | |
|---|---|---|---|
| 7,652,313 B2 | 1/2010 | Ellis-Monaghan et al. | |
| 7,652,557 B2 | 1/2010 | Kantrowitz et al. | |
| 7,791,481 B2 | 9/2010 | Landt et al. | |
| 8,205,800 B2 | 6/2012 | Addy | |
| 8,924,023 B2 | 12/2014 | Akpan | |
| 9,108,006 B2 | 8/2015 | Jensen et al. | |
| 2001/0051766 A1* | 12/2001 | Gazdzinski | A61B 1/00016 600/309 |
| 2004/0020173 A1 | 2/2004 | Cho | |
| 2004/0166140 A1 | 8/2004 | Santini, Jr. et al. | |
| 2004/0230182 A1 | 11/2004 | Heruth et al. | |
| 2005/0240370 A1 | 10/2005 | Diorio et al. | |
| 2006/0115323 A1 | 6/2006 | Coppeta et al. | |
| 2006/0127097 A1 | 6/2006 | Obrea et al. | |
| 2007/0015549 A1 | 1/2007 | Hernandez et al. | |
| 2007/0103311 A1 | 5/2007 | Kippelen et al. | |
| 2007/0273485 A1 | 11/2007 | Balachandran et al. | |
| 2008/0088417 A1 | 4/2008 | Smith et al. | |
| 2009/0099553 A1 | 4/2009 | Langereis et al. | |
| 2009/0306633 A1* | 12/2009 | Trovato | A61B 1/041 604/891.1 |
| 2010/0128749 A1 | 5/2010 | Amann et al. | |
| 2010/0182160 A1 | 7/2010 | Lu | |
| 2010/0328043 A1 | 12/2010 | Jantunen et al. | |
| 2011/0053503 A1 | 3/2011 | Witschnig et al. | |
| 2011/0108616 A1 | 5/2011 | Wang | |
| 2011/0205134 A1 | 8/2011 | Blumberg, Jr. | |
| 2011/0215156 A1 | 9/2011 | Johnson, II et al. | |
| 2012/0032785 A1 | 2/2012 | Kamata | |
| 2012/0161338 A1 | 6/2012 | Lowenthal et al. | |
| 2012/0234922 A1 | 9/2012 | Sample et al. | |
| 2012/0245565 A1 | 9/2012 | Shachar et al. | |
| 2013/0030763 A1 | 1/2013 | Mazzillo | |
| 2013/0206837 A1 | 8/2013 | Szu | |
| 2015/0272830 A1* | 10/2015 | Iordanov | A61J 7/0481 221/1 |
| 2016/0074323 A1 | 3/2016 | Chey et al. | |
| 2017/0325746 A1* | 11/2017 | Niichel | A61B 5/6861 |

FOREIGN PATENT DOCUMENTS

| | | |
|---|---|---|
| CN | 202711296 U | 1/2013 |
| CN | 203562013 U | 4/2014 |
| CN | 103955736 A | 7/2014 |
| JP | 2013061888 A | 4/2013 |
| KR | 20090098472 A | 9/2009 |
| WO | 2008091826 A1 | 7/2008 |
| WO | 2009064402 A1 | 5/2009 |
| WO | 2009107136 A2 | 9/2009 |

OTHER PUBLICATIONS

Knowles, "New Product: Ultrasonic MEMS Microphone," http://www.knowles.com/eng/Newsroom/New-product-Ultrasonic-MEMS-Microphone, Feb. 1, 2016, 2 pages.
R. Colin Johnson, "MEMS Mics Taking Over, Tasks Once Performed by Specialized Chips," EETimes, http://www.eetimes.com/document.asp?doc_id=1324827, Dec. 2, 2014, 3 pages.
Focused Ultrasound Foundation, "Overview," http://www.fusfoundation.org/the-technology/overview, Feb. 1, 2016, 2 pages.
List of IBM Patents or Patent Applications Treated as Related.
S. Roy et al., "RFID: From Supply Chains to Sensor Nets," Proceedings of the IEEE, Jul. 2010, pp. 1583-1592, vol. 98, No. 9.
M. Buckner et al., "GPS and Sensor-Enabled RFID Tags," Unclassified Document, Oak Ridge National Laboratory, http://www.ornl.gov/webworks/cppr/y2001/pres/118169.pdf, 2001, 5 pages.
A.P. Sample et al., "Design of a Passively-Powered, Programmable Sensing Platform for UHF RFID Systems," IEEE international Conference on RFID, Mar. 2007, pp. 149-156.

* cited by examiner

500

500

600

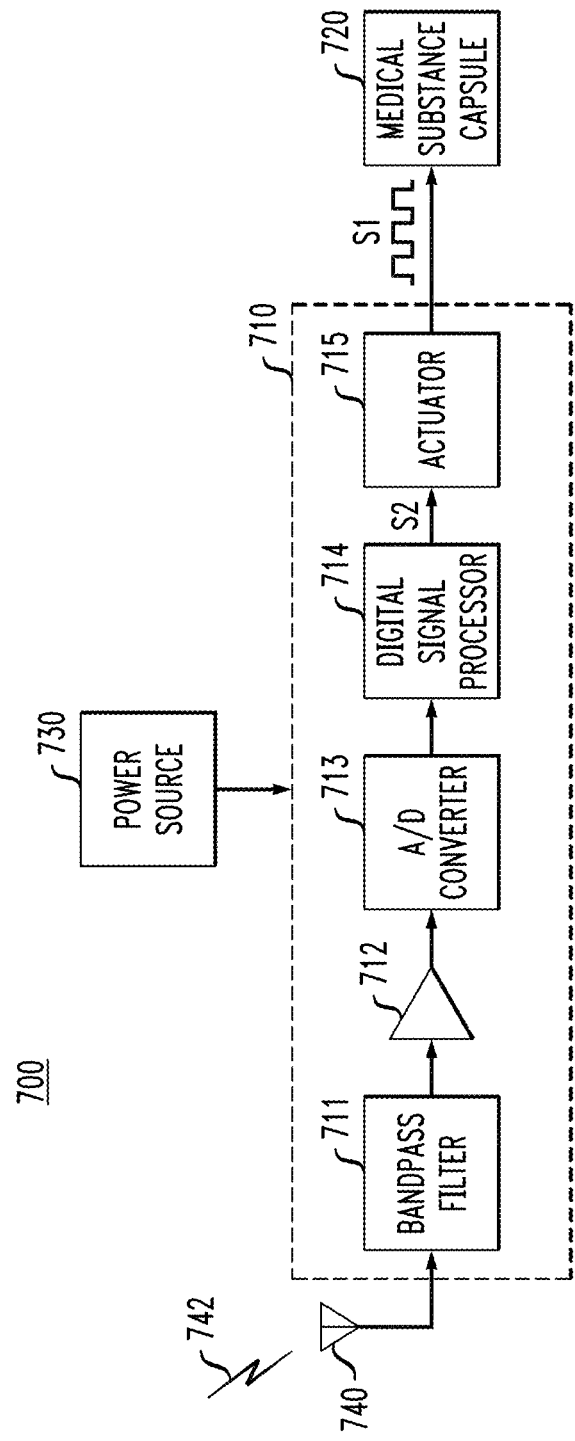

800

900

1000

1200

1400

1500

MICROCHIP MEDICAL SUBSTANCE DELIVERY DEVICES

TECHNICAL FIELD

This disclosure generally relates to microchip medical substance delivery devices and methods for controlled delivery of substances such as drugs and medication.

BACKGROUND

In recent years, there has been significant research and development in the biomedical field with regard to drug delivery devices and, in particular, implantable bio-compatible microchip drug delivery devices. In general, an implantable microchip drug delivery device includes an array of micro-scale reservoirs that are formed in a substrate. The reservoirs are filled with certain medications/drugs that are contained within the reservoirs using releasable membrane structures. The microchip drug delivery devices are designed with various types of actuation mechanisms that allow the contents of the reservoirs to be automatically released (via the releasable membrane structures) either continuously, periodically or "on demand" by an individual (e.g., doctor or patient). These actuation mechanisms generally include passive or high-power active release mechanisms.

SUMMARY

Embodiments of the invention include microchip medical substance delivery devices and methods for controlled delivery of substances such as drugs and medication using low-power active release mechanisms.

For example, one embodiment includes a microchip medical substance delivery device. The device includes a control system, and a medical substance capsule. The medical substance capsule comprises a medical substance contained with a reservoir, and a release structure configured to release the medical substance from within the reservoir in response to an activation signal generated by the control system. The control system comprises a wireless signal receiving element, a processor, an actuator circuit, and a power supply source. The wireless signal receiving element is configured to capture a wireless signal. The processor is configured to detect a presence of an activation code embedded within the captured wireless signal, and generate an actuator control signal in response to the detection of the activation code within the captured wireless signal. The actuator circuit is configured to generate the activation signal in response to the actuator control signal generated by the processor. The power supply source is configured to provide DC (direct current) power voltage to active components of the control system.

Another embodiment includes a method for delivery of a medical substance. The method comprises: receiving a wireless signal by a microchip medical substance delivery device that is disposed within a body of an individual, wherein microchip medical substance delivery device comprises a control system, and a medical substance capsule, the medical substance capsule comprising a medical substance contained within a reservoir, and a release structure that is configured to release the medical substance from within the reservoir in response to an activation signal generated by the control system; processing, by the control system, the received wireless signal to detect a presence of an activation code embedded within the captured wireless signal; generating, by the control system, an actuator control signal in response to the detection of the activation code within the captured wireless signal; generating, by the control system, the activation signal in response to the actuator control signal; applying the activation signal to the medical substance capsule to activate the release structure and release the medical substance from within the reservoir of the medical substance capsule.

Other embodiments of the invention will be described in the following detailed description of embodiments, which is to be read in conjunction with the accompanying drawings.

BRIEF DESCRIPTION OF THE DRAWINGS

FIG. 7 is a block diagram of a control system which is configured to control the activation of a medical substance capsule device, according to an embodiment of the invention.

DETAILED DESCRIPTION

Embodiments of the invention will now be discussed in further detail with regard to microchip medical substance delivery devices and methods for controlled delivery of medical substances such as drugs and medication using low-power active release mechanisms. It is to be understood that the various layers, structures, and regions of devices shown in the accompanying drawings are not drawn to scale, and that one or more layers, structures, and regions of a type commonly used in microchip substance delivery devices may not be explicitly shown in a given drawing. This does not imply that the layers, structures, and regions not explicitly shown are omitted from the actual microchip substance delivery devices. Moreover, the same or similar reference numbers used throughout the drawings are used to denote the same or similar features, elements, or structures, and thus, a detailed explanation of the same or similar features, elements, or structures will not be repeated for each of the drawings.

Figure 1:
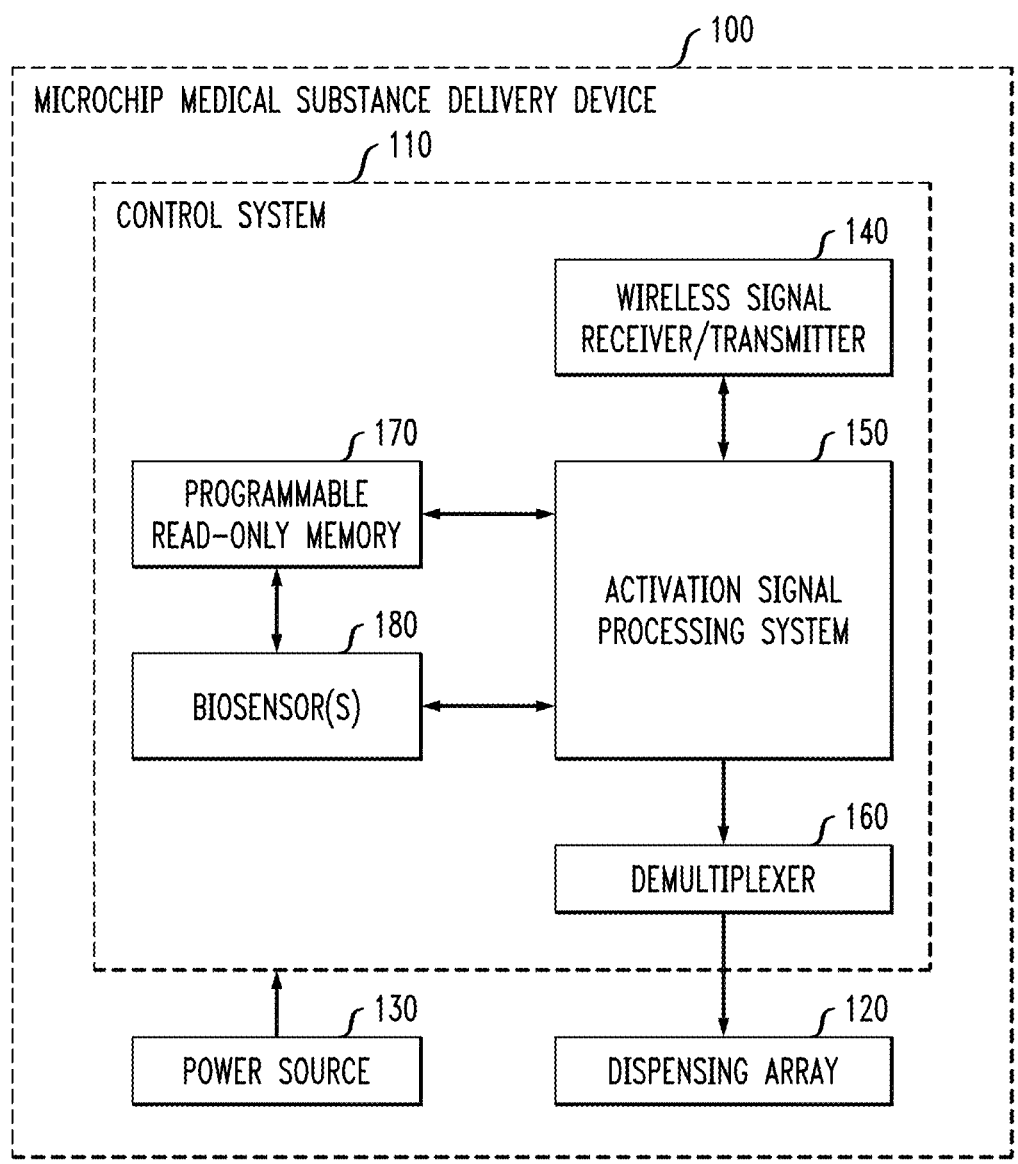
FIG. 1 is a schematic block diagram of a microchip medical substance delivery device according to an embodiment of the invention.

FIG. 1 is a schematic block diagram of a microchip medical substance delivery device 100 according to an embodiment of the invention. The medical substance delivery device 100 comprises a control system 110, a dispensing array 120, and a power source 130. The control system 110 comprises a wireless signal receiver/transmitter 140, an activation signal processing system 150, a demultiplexer 160, a programmable ROM 170, and one or more biosensors 180. The dispensing array 120 comprises an array of electronically-addressable "medical substance capsules", comprising an array of micro-scale reservoirs that are formed in a substrate. Each reservoir is filled with a medical substance (e.g., medication, drugs, hormones, etc.) that is contained within the reservoir using a seal and lid (or membrane) structure.

In this regard, each "medical substance capsule" of the dispensing array 120 comprises reservoir filled with a medical substance, and an associated release structure (e.g., seal/lid structure) which is configured to contain the medical substance within the reservoir, and then release the medical substance from within the reservoir in response to the release structure being activated/actuated by the control system 110. There are various types of release structures with different activation/actuation mechanisms, which can be implemented in conjunction with medical substance capsule devices to allow the contents of the reservoirs to be released either continuously, periodically or "on demand" by an individual (e.g., doctor or patient). Example embodiments of "medical substance capsule" structures and associated activation/actuation mechanisms, which can be used to implement the dispensing array 120, will be discussed in further detail below with reference to FIGS. 2, 3A/3B, 4A/4B, 5, and 6A/6B.

It is to be noted that the exemplary microchip substance delivery devices and medical substance capsule devices described herein can be fabricated using standard MEMS (Micro-Electro-Mechanical-Systems) fabrication techniques, as well as wafer-level 3D fabrication and integration, and CMOS processing techniques. In particular, these techniques can be used to construct a device substrate having array of micro reservoirs to store deliverable substances (such as drugs or medications), as well as construct release structures to seal the deliverable substances within the cavities of the device substrate, and build the control circuitry to control the activation/actuation of the release structures. Indeed, various components and structures of microchip substance delivery devices according to embodiments of the invention can be fabricated using a combination of standard processes, namely semiconductor lithography, MEMs processes, and low-temperature wafer-to-wafer three-dimensional silicon processes, and using standard materials and structures that are compatible with back-end-of-the-line (BEOL) processing, wafer bonding, wafer thinning, and wafer transfer processes.

The activation signal processing system 150 is configured to generate and output select control signals to the demultiplexer 160. The demultiplexer 160 is configured to selectively activate one or more of the discrete medical substance capsules of the dispensing array 120, in response to a select control signal output from the activation signal processing system 150. The activation signal processing system 150 selectively activates one or more of the discrete medical substance capsules by outputting control pulses (e.g., voltage or current pulses), which are generated by an actuation circuit of the activation signal processing system 150, to break, melt, rupture, etc. the seal and/or lid structure of a selected medical substance capsule, and thereby release the medical substance from within the reservoir of the selected medical substance capsule.

In one embodiment, the activation signal processing system 150 generates control signals to activate the release of medical substances from the medical substance capsules of the dispensing array 120 according to a programmed schedule stored in the programmable ROM 170. In another embodiment, activation signal processing system 150 generates control signals to activate the release of medical substances from the medical substance capsules of the dispensing array 120 according to control signals output from one or more of the biosensors 180 which automatically detect physiological conditions in which required doses of a given drug or medication are to be administered. For example, the biosensor(s) 180 can be configured to detect a localized infection, wherein detection of the localized infection causes the activation signal processing system 150 to release antibiotic substances from one or more of the medical substance capsules. In yet another embodiment, the activation signal processing system 150 generates control signals to activate substance release in response to activation control signals which are captured by the wireless signal receiver 140, and which are transmitted from a remote source operated by a doctor or individual using or controlling the microchip medical substance delivery device 100.

In one embodiment of the invention, the programmable ROM 170 comprise a one-time field programmable fuse memory, which can be programmed to store a predefined activation code and other instructions to control operation of the microchip medical substance delivery device 100. In another embodiment of the invention, the programmable ROM 170 may implement a multiple read/write memory device framework.

Various components of the control system 110 comprise integrated circuits that are integrally formed on the same microchip substrate in which the dispensing array 120 is formed. The circuitry of the control system 110 can be constructed using standard silicon integrated circuit technology. The power source 130 is configured to provide a DC bias voltage (e.g., VDD) for operating the various components of the control system 110. In one embodiment of the invention, the power source 130 can be implemented as an internal power source, such as a bio-compatible thin-film battery or capacitor-based power supply, which is integrated as part of the microchip medical substance delivery device 100. In this embodiment, while the battery size, material, and packaging requirements limit the energy capacity of the power source 130, the energy requirements for the medical substance release are preferably minimized using low-power release mechanisms as will be discussed below. In other embodiments, the power source 130 can be implemented using circuitry that is configured to generate a DC bias voltage from wireless signals (e.g., RF or optical signals) that are received by the wireless signal receiver 140 from an external source.

It is to be understood that the microchip medical substance delivery device 100 can be utilized in various types of drug delivery applications. For example, the microchip medical substance delivery device 100 can be positioned in a target location within an individual's body by implantation (e.g., under skin, near tear duct, etc.). Implantation is beneficial when the microchip medical substance delivery device 100 is to remain within the body to administer multiple doses of drugs/medications over a relatively long period of time. In other applications, the microchip medical substance delivery device 100 can be implemented as part of an ingestible device (e.g., swallowable pill) which can be swallowed by an individual. In this application, drug delivery can be provided over a shorter time period that it takes for the ingestible device to pass through the individual's digestive tract. In the case of an ingestible device that moves through the digestive tract, the medication delivery can be done accurately by using a focused ultrasonic beam to trigger the control system 110 when the ingested medical substance delivery device is located in a target area (e.g., stomach, intestine, etc.). Similarly, for a medical substance delivery device that is injected into the blood stream of an individual, the medication delivery can be done accurately by using a focused ultrasonic beam or any other focused wireless technology (e.g., RF, mmwave, etc.) to trigger the control system 110 when the medical substance delivery device reaches a target location (e.g., organ). Moreover, in other applications, the microchip medical substance delivery device 100 can be implemented as a wearable device (e.g., a transdermal device or a component of a transdermal device) that is configured to deliver drugs through an individual's skin.

Figure 2:
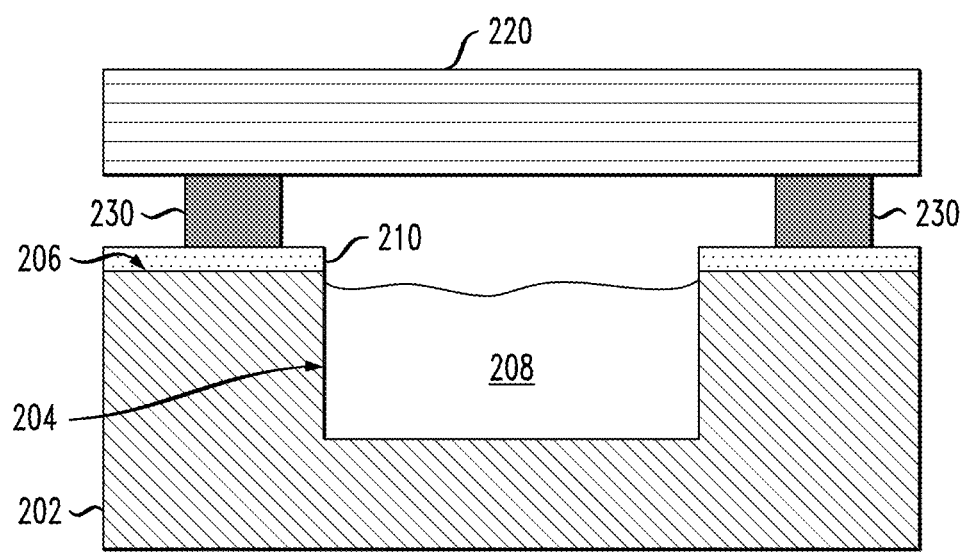
FIG. 2 is a high level schematic illustration of a medical substance capsule device having a low-power release mechanism, which can be implemented with the microchip medical substance delivery device of FIG. 1 according to an embodiment of the invention.

FIG. 2 is a high level schematic illustration of a medical substance capsule having a low-power release mechanism, which can be implemented with the microchip medical substance delivery device of FIG. 1 according to an embodiment of the invention. In particular, FIG. 2 schematically illustrates a medical substance capsule 200 which can be implemented as part of the dispensing array 120 of FIG. 1. The medical substance capsule device 200 comprises a substrate 202 and a cavity 204 formed in a surface 206 of the substrate 202. The cavity 204 is filled with a deliverable medical substance 208 such as a medication or drug in liquid or solid form, for example. The substrate 202 further comprises an insulating layer (which is part of a BEOL (back end of line) structure) formed on the surface 206 of the substrate 202. The medical substance capsule 200 further comprises a lid structure 220 (or membrane) disposed on the substrate 202 covering an opening of the cavity 204, and a seal 230 disposed between the lid structure 220 and the substrate 202. The seal 230 surrounds the opening of the cavity 204. The seal 230 and the membrane 220 are configured to enclose the cavity 204 and retain the medical substance 208 within the cavity 204.

In FIG. 2, while only one cavity 204 is shown for ease of illustration, it is to be understood that the substrate 202 may be formed with an array of cavities (e.g., dispensing array 120) comprising, for example, hundreds of cavities, which serve as reservoirs for holding the same type or a combination of different types of deliverable medical substances. In particular, in one embodiment, the substrate 202 illustrated in FIG. 2 represents a portion of the substrate of the microchip medical substance delivery device 100 of FIG. 1, which comprises the various integrated circuit components of the control system 110 and the dispensing array 120 formed on the substrate 202.

Various low-power release mechanisms can be implemented in conjunction with the medical substance capsule 200 of FIG. 2 to release the medical substance 208 from within the cavity 204. These release mechanisms include, for example, melting or otherwise breaking the seal 230 to release the lid structure 220, or rupturing the lid structure 220 to release the medical substance 208. Example embodiments of low-power release mechanisms, which can be implemented with medical substance capsules in the dispensing array 120 of FIG. 1, are described, for example, in U.S. patent application Ser. No. 14/928,508, filed on Oct. 30, 2015, entitled "Delivery Device Including Reactive Material for Programmable Discrete Delivery of a Substance," as well as U.S. patent application Ser. No. 14/483,278, filed on Sep. 11, 2014, entitled "Microchip Substance Delivery Devices Having Low Power Electromechanical Release Mechanisms," both of which are commonly assigned and incorporated herein by reference.

In particular, U.S. patent application Ser. No. 14/928,508 discloses low-power release mechanisms that are based on propagating exothermic reactions in reactive material structures (e.g., multi-layered nano-laminate metallic film structures). By way of example, a reactive material structure can be fabricated with two or more alternating dissimilar layers of materials such as Si—Nb, Cu—Pd, Al—Ti, Si—Co, Al—Ni, Al—Pt, or Al—Pd, for example. Exothermic reactions can self-propagate rapidly in a multilayered reactive material structure when the reactive material structure is "ignited" using a certain stimulus. The properties of these exothermic reactions depend on various factors, such as, e.g., a heat of reaction of the materials, an average atomic diffusion distance, and a degree of intermixing at the layer interfaces. To enable an exothermic reaction with sufficient energy release and self-propagation, the material layers are preferably formed thin with low or no intermixing or diffusion between the material layers during fabrication, which reduces the energy needed to initiate a reaction. For typical deposition technologies, the thickness of the individual layers is between about 5 nanometers (nm) and 50 nm, and preferably greater than about 10 nm to avoid intermixing and reaction during layer deposition.

Various ignition techniques can be implemented to ignite a reactive material structure, including, for example, electrical, thermal, magnetic, optical, and mechanical ignition techniques. In particular, in at least one embodiment, a reactive material structure is thermally ignited by applying an electric current or voltage to a heater electrode disposed in close proximity to the reactive material structure, which causes the heater electrode to generate a level of thermal energy that is sufficient to ignite the reactive material structure. In another embodiment, a low power electric current or voltage is applied directly to the reactive material structure to ignite a self-propagating reaction. A reactive material structure can be designed to ignite a self-propagating reaction with low ignition currents (e.g., as low as 3.3 pA for 100 ns) and low thermal ignition temperatures (e.g. as low as 177 degrees Celsius).

Figure 3A:
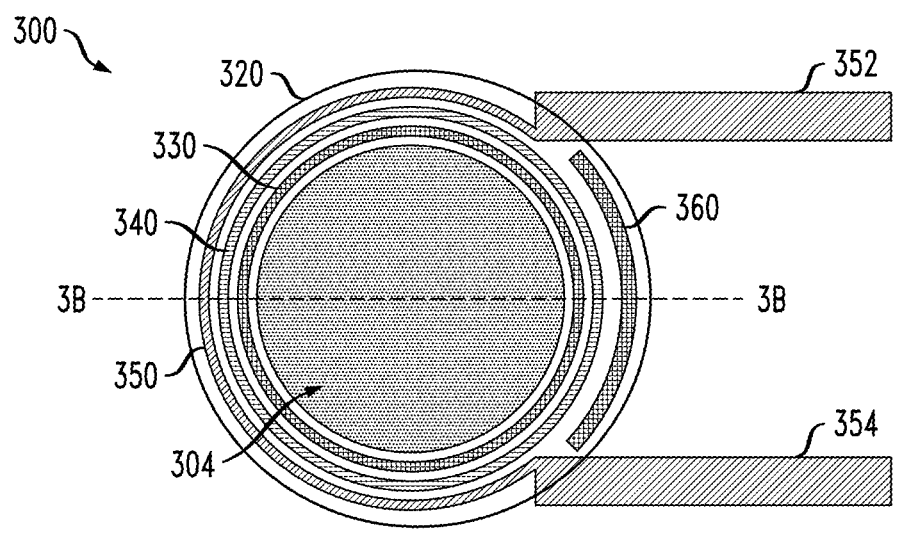
FIGS. 3A and 3B schematically illustrate a medical substance capsule device having a low-power release mechanism, which can be implemented with the microchip medical substance delivery device of FIG. 1 according to another embodiment of the invention.
Figure 3B:
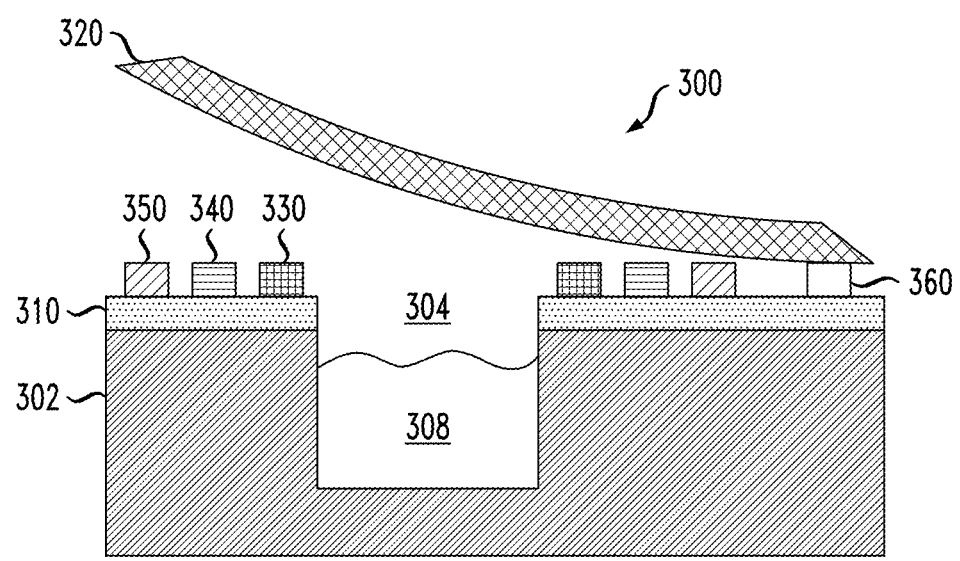

FIGS. 3A and 3B schematically illustrate a medical substance capsule device having a low-power release mechanism, which can be implemented with the microchip medical substance delivery device of FIG. 1 according to another embodiment of the invention. In particular, FIGS. 3A and 3B schematically illustrate an embodiment of a medical substance capsule device 300 which is based on propagating an exothermic reaction in reactive material structure, as disclosed and described in further detail in U.S. patent application Ser. No. 14/928,508. FIG. 3A is a schematic top plan view of the medical substance capsule device 300 and FIG. 3B is a schematic cross-sectional view of the medical substance capsule device 300 taken along line 3B-3B in FIG. 3A. FIG. 3B illustrates the medical substance capsule device 300 in an "activated" state.

As shown in FIGS. 3A/3B, the medical substance capsule device 300 comprises a substrate 302 and a cavity 304 formed in a surface of the substrate 302. The cavity 304 is filled with a deliverable medical substance 308 such as a medication or drug in liquid or solid form, for example. An insulating layer 310 is formed on a surface of the substrate 302. The medical substance capsule device 300 further comprises a stressed lid structure 320, a seal 330, a reactive material structure 340, a resistive heater 350, resistive heater contacts 352/354, and a hinge structure 360. The seal 330 surrounds the opening of the cavity 304. The seal 330 may be formed of a low melting point material such as solder, oxide or a polymer. The seal 330 and the stressed lid structure 320 are configured to enclose the cavity 304 and retain the medical substance 308 within the cavity 304.

The medical substance capsule device 300 implements a low-power release mechanism which involves heating the reactive material structure 340 using heat generated by the resistive heater 350 to ignite a self-propagating exothermic reaction in the reactive material structure 340. In particular, the control system 110 (FIG. 1) generates and applies a control voltage or control current to the resistive heater 350 via the contacts 352/354, which causes the resistive heater 350 to locally heat a least a portion of the reactive material structure 340 that is disposed adjacent to the resistive heater 350, and thereby ignite a self-propagating exothermic reaction in the reactive material structure 340. The resistive heater 350 comprises a thinner profile or smaller surface area, as compared to the heater contacts 352/354, which facilitates localized heating of the area adjacent to the resistive heater 350. The combined thermal energy generated by the resistive heater 350 and the exothermic reaction of the reactive material structure 340 serves to melt or otherwise degrade the seal 330, thereby "releasing" the stressed lid structure 320, as shown in FIG. 3B.

In particular, in one embodiment, the stressed lid structure 320 comprises one or more material layers formed in a pre-stressed state to facilitate a "peel back" of the released portion of the stressed lid structure 320, while the stressed lid structure 320 remains attached to the hinge structure 360. For example, the stressed lid structure 320 may include a first layer of material that is formed in a state of internal compressive stress, and a second layer of material that is formed in a state of internal tensile stress, which causes the stressed lid structure 320 to curl or otherwise peel back when released (as shown in FIG. 3B) upon melting at least a portion of the seal 330 due to the local heating thereof by the resistive heater 350 and the exothermic reaction of the reactive material structure 340. The hinge structure 360 can be formed of the same material that is used to form the seal 330. In a suitably-designed structure, the heat that is generated to melt the seal 330 is substantially confined to the region containing the seal 330 and the reactive material structure 340. As such, the hinge structure 360 is not thermally degraded, and the stressed lid 320 remains attached to the hinge structure 306 (i.e., the stressed lid 320 does not disconnect from the substrate 302).

In another embodiment, a medical substance capsule device can be implemented, which is similar to the embodiment shown in FIGS. 3A/3B, but which utilizes a biocompatible and biodegradable lid structure and does not include the hinge structure 360. In this embodiment, upon release of the biocompatible and biodegradable lid structure, the lid structure is released into the body (and not remain attached to the substrate), wherein the biocompatible and biodegradable lid structure degrades within the body over time.

In another embodiment, a medical substance capsule device can be implemented, which is similar to the embodiment shown in FIGS. 3A/3B, but wherein the seal 330 and reactive material structure 340 are disposed in a stack structure, with the resistive heater 350 surrounding at least a portion of the stacked seal/reactive material structure. In this embodiment, the reactive material structure 340 can be heated to its ignition temperature via the resistive heater 350, wherein the self-propagating exothermic reaction of the reactive material structure 340 melts or otherwise degrades the seal 330 to effect release of a lid structure (e.g., partial release with hinge mechanism, or complete release of a biocompatible and biodegradable lid structure).

Figure 4:
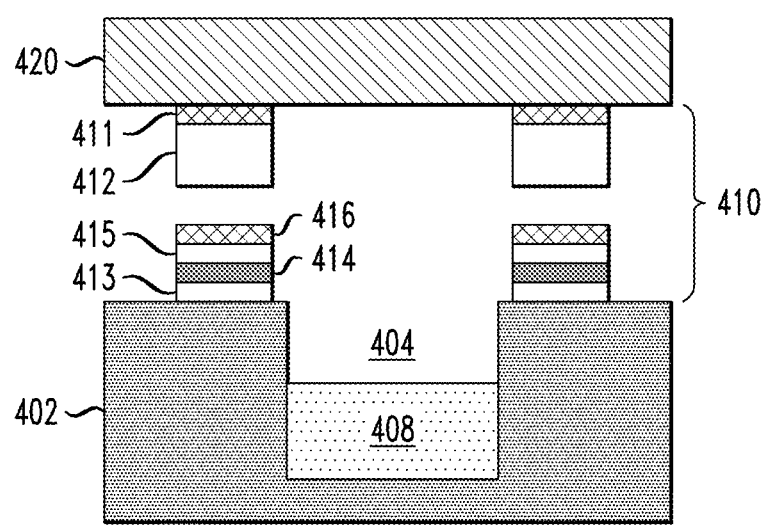
FIG. 4 schematically illustrates a medical substance capsule device having a low-power release mechanism, which can be implemented with the microchip medical substance delivery device of FIG. 1 according to an embodiment of the invention.

FIG. 4 schematically illustrates a medical substance capsule device having a low-power release mechanism, which can be implemented with the microchip medical substance delivery device of FIG. 1 according to another embodiment of the invention. In particular, FIG. 4 schematically illustrates an embodiment of a medical substance capsule device 400 which is based on propagating an exothermic reaction in reactive material structure, as disclosed and described in further detail in U.S. patent application Ser. No. 14/928,508. As shown in FIG. 4, the medical substance capsule device 400 comprises a substrate 402 and a cavity 404 formed in a surface of the substrate 402. The cavity 404 is filled with a deliverable medical substance 408 such as a medication or drug in liquid or solid form, for example. The medical substance capsule 400 further comprises a seal structure 410 and a lid structure 420, wherein the seal structure 410 comprises stack structure of different material layers including a reactive material layer.

In particular, the seal structure 410 comprises a first layer 411 formed on the lid structure 420, wherein the first layer 411 comprises a solder UBM (under bump metallization) or adhesion layer. A second layer 412 (e.g., a solder, polymer or oxide bond layer) is formed on the first layer 411. A metal or adhesion layer 413, a reactive material layer 414, an insulator layer 415 (e.g., silicon dioxide ($SiO_2$)) and a second solder or adhesion layer 416 are sequentially formed on the substrate 402 (e.g., silicon substrate). The lid structure 400 can be released using a resistive heater to thermally ignite the reactive material structure 414 and break the seal structure 410, or to electrically ignite the reactive material layer 414 by direct application of an electrical activation signal (e.g., voltage or current signal). The insulator layer 415 serves to restrict heat flow from the reactive material layer 414 into the lid structure 420, or in the case of electrical activation, restricts an electrical current from flowing into the lid structure 420.

Figure 5A:
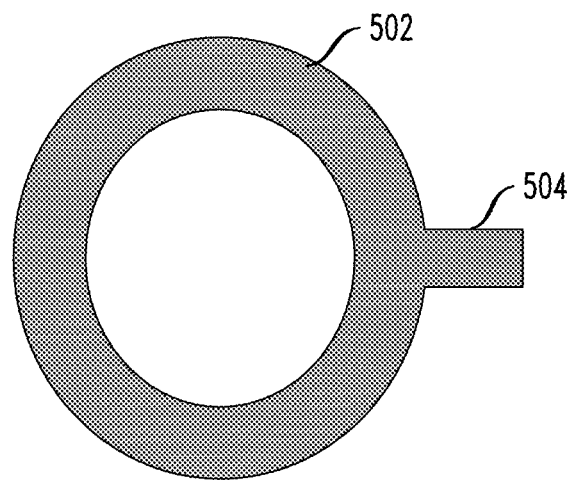
FIGS. 5A and 5B schematically illustrate a reactive material structure having an electrical ignition mechanism, according to an embodiment of the invention.
Figure 5B:
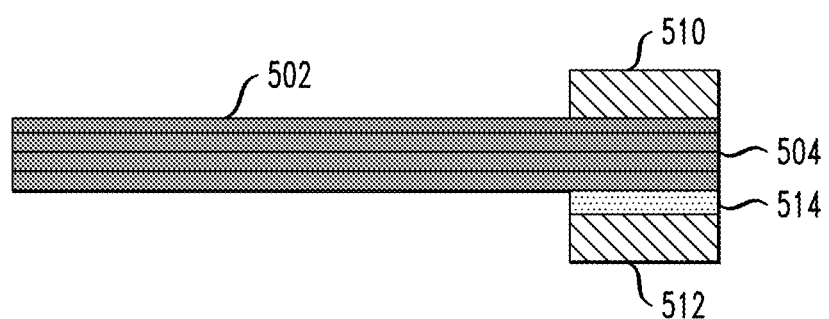

FIGS. 5A and 5B schematically illustrates a reactive material structure having an electrical ignition mechanism, according to an embodiment of the invention. In particular, FIG. 5A is a schematic top plan view of a reactive material structure 500 comprising a circular-shaped portion 502 and an ignition tab 504. In one embodiment, the reactive material structure 500 comprises a multi-layered structure with two or more alternating dissimilar layers of materials, as discussed above. FIG. 5B is a schematic side view of the reactive material structure 500 with an electrical ignition structure 510/512/514 that is disposed on the ignition tab 504. The electrical ignition structure 510/512/514 comprises a first electrode 510, a second electrode 512, and a thin layer of dielectric material 514. The layer of dielectric material 514 is disposed between the ignition tab 504 and the second electrode 512.

In this structural configuration, the control system 110 (FIG. 1) generates and applies an activation signal (e.g., voltage pulse, current pulse, voltage pulse stream, current pulse stream) to the first and second electrodes 510 and 512 to cause a breakdown of the thin layer of dielectric material 514, which in turn, creates a high current density pulse that is applied to the ignition tab 504. This high current density pulse is sufficient to ignite an exothermic reaction of the reactive material of the ignition tab 504, which then propagates to and around the circular-shaped portion 502 of the reactive material structure 500.

In one embodiment, the reactive material structure 500 shown in FIGS. 5A/5B can be implemented in a medical substance capsule device having a framework such as shown in FIGS. 3A/3B, wherein the reactive material structure 500 surrounds the seal structure 330, and wherein the electrode structure 350/352/354 does not serve as a resistive heater, but rather is patterned to form the first and second electrodes 510 and 512 on the ignition tab 504, to apply an activation signal to initiate a self-propagating exothermic reaction in the ignition tab 504. In another embodiment, the reactive material structure 500 shown in FIGS. 5A/5B can be implemented in a medical substance capsule device having a framework such as shown in FIG. 4, wherein the reactive material structure 500 is part of the stack of layers (e.g., reactive material layer 414) that form the seal structure 410.

Figure 6A:
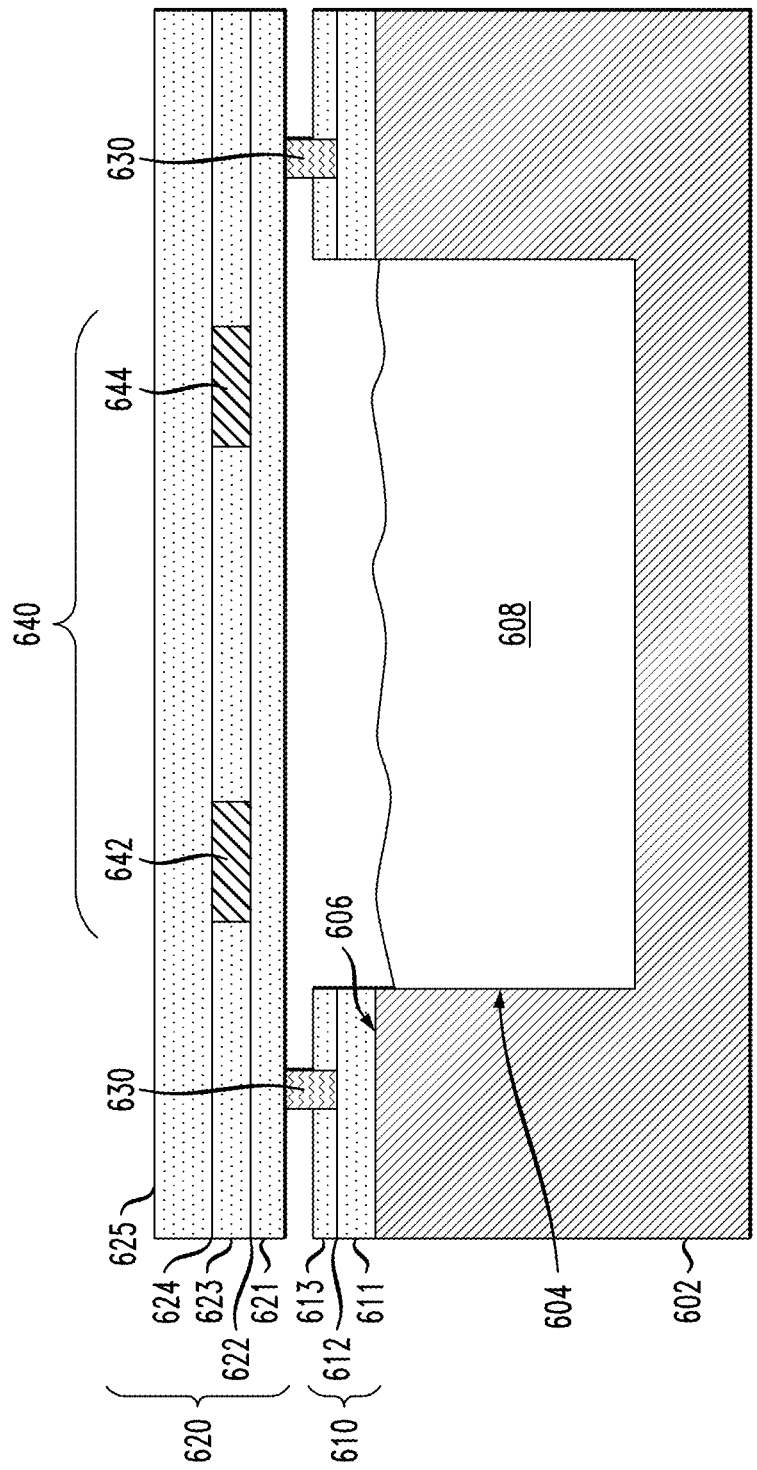
FIGS. 6A and 6B schematically illustrate a medical substance capsule device having a low-power release mechanism, which can be implemented with the microchip medical substance delivery device of FIG. 1 according to another embodiment of the invention.
Figure 6B:
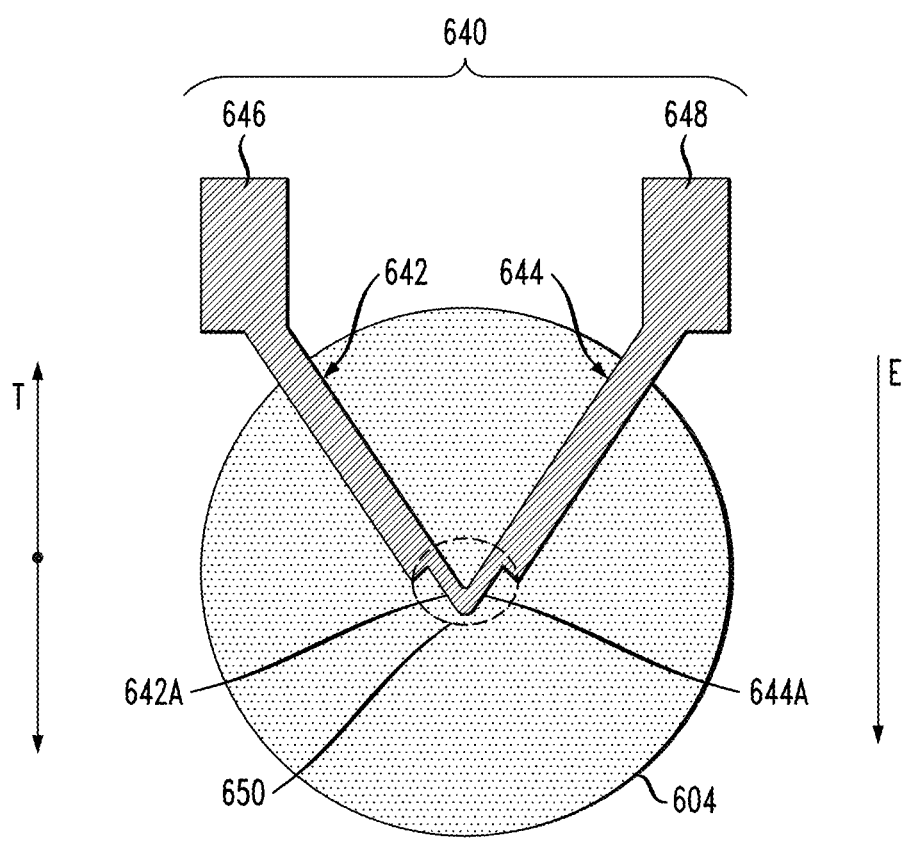

FIGS. 6A and 6B schematically illustrate a medical substance capsule device having a low-power release mechanism, which can be implemented with the microchip medical substance delivery device of FIG. 1 according to another embodiment of the invention. In particular, FIGS. 6A and 6B schematically illustrates an embodiment of a medical substance capsule device 600 which is based on a low-power electromechanical release mechanism, as disclosed and described in further detail in U.S. patent application Ser. No. 14/483,278. In particular, FIG. 6A is a schematic side view of a medical substance capsule device 600, and FIG. 6B is a schematic top plan view of a portion of the medical substance capsule device 600 of FIG. 6A. As shown in FIG. 6A, the medical substance capsule device 600 comprises a substrate 602 and a cavity 604 formed in a surface 606 of the substrate 602. The cavity 604 is filled with a deliverable substance 608 such as a medication or drug in liquid or solid form, for example. The substrate 602 further comprises a plurality of insulating layers 610 (which are part of a BEOL structure) formed on the surface 606 of the substrate 602. In the example embodiment of FIG. 6A, the insulating layers 610 include, for example, a stack of layers including a silicon dioxide layer 611, a silicon nitride layer 612, and a silicon dioxide layer 613.

The medical substance capsule device 600 further comprises a membrane 620 (lid structure) disposed on the substrate 602 covering an opening of the cavity 604, and a seal 630 disposed between the membrane 620 and the surface 606 of the substrate 602. The seal 630 surrounds the opening of the cavity 604. The seal 630 and the membrane 620 are configured to enclose the cavity 604 and retain the substance 608 within the cavity 604.

In addition, as collectively shown in FIGS. 6A and 6B, the medical substance capsule device 600 further comprises an electrode structure 640 that is integrally formed as part of the membrane 620. As specifically shown in FIG. 6A, in one embodiment of the invention, membrane 620 is formed of multiple layers of insulating material including, for example, thin silicon dioxide layers 621, 623, 625, and thin silicon nitride layers 622 and 624 disposed between the silicon dioxide layers 621, 623, 625. The electrode structure 640 comprises a patterned layer of a metallic material such as copper, having electrode elements formed in one or more of the silicon dioxide layers 621, 623 and 625. The electrode structure 640 is configured to locally heat a portion 650 of the membrane 620 in response to a control voltage applied to the electrode structure 640 (via control circuitry as discussed herein). This localized heating of the membrane 620 creates a mechanical stress in the locally heated portion 650 of the membrane 620 which is sufficient to cause a rupture in the locally heated portion 650 of the membrane 620 and release the substance 608 from within the cavity 604.

More specifically, FIG. 6B is a partial top plan view that illustrates an exemplary pattern of the electrode structure 640 as formed within the silicon dioxide layer 623 of the membrane 620, as well as position of the electrode structure 640 with regard to a perimeter of the opening of the cavity 604. In the embodiment shown in FIG. 6B, the electrode structure 640 comprises a V-shaped electrode 642/644, a first contact 646 and a second contact 648. The V-shaped electrode 642/644 comprises a first leg 642 and a second leg 644. The first and second contacts 646 and 648 serve as anode/cathode contacts that receive a control voltage from control circuitry which is connected to the first and second contacts 646 and 648 using wiring structures such as metallic vias and traces that are formed through and within other layers of the membrane 620 and/or other metallization that is formed as part of the BEOL 610 of the microchip substance delivery device 600.

The first leg 642 extends from the first contact 646 and includes an end portion 642A that is thinner in width than the width of the first leg 642. Similarly, the second leg 644 extends from the second contact 648 and includes an end portion 644A that is thinner in width than the width of the second leg 642. The end portions 642A and 644A of the first and second legs 642 and 644 form an "apex" portion of the V-shaped electrode 642/644 which is configured to provide localized heating of the portion 650 of the membrane 620. More specifically, when a control voltage is applied to the first and second contacts 646 and 648, the current flow through the V-shaped electrode 642/644 will have a higher current density in the apex region 642A/644A because of the thinner width metallization pattern and the angled shape of the apex region 642A/644A. This higher current density in the apex region 642A/644A results in a high thermal density in the locally heated portion 650 of the membrane 620 surrounding the apex region 642A/644A. This localized high thermal density causes a mechanical stress in the locally heated portion 650 of the membrane 620 which is sufficient to rupture the membrane 620.

More specifically, the electrode structure 640 shown in FIG. 6B provides a low-energy release mechanism with precise control of the release location on the membrane 620. When properly designed, sufficient heat can be generated in the locally heated region 650 of the membrane 620 by the application of a pulsed control voltage. Indeed, since the thinner profile apex region 642A/644A focuses current density in the locally heated region 650, the application of a pulsed voltage is sufficient to cause significant heating and expansion of the insulating material in the locally heated region 650 of the membrane 620 and induce membrane rupture in the locally heated region 650. The high current density flowing through the apex region 642A/644A of the electrode 640 confines the high thermal density to the small local region 650 of the membrane 620 to provide a more precise control of the rupturing location of the membrane 620 due to the increased localized energy density in the locally heated portion 650.

In one embodiment of the invention, the electrode structure 640 is designed so that the locally heated portion 650 of the membrane 620 has a lateral dimension that is less than about two times a thickness of the membrane 620. In other words, to achieve low-power release, the region of membrane 620 which is locally heated is restricted in size to an area much smaller than the size of the cavity 604 (which is in contrast to other release schemes that are designed to heat an area of the membrane which is the same as the area of the cavity opening). The size of the locally heated portion 650 of the membrane 620 (in relation to the thickness of the membrane 620) will vary depending on the material(s) used to form the membrane 620 and whether the membrane 620 is formed in a non-stressed state or a stressed state.

More specifically, in one embodiment of the invention, the membrane 620 can be formed in a non-stressed state (e.g., no tensile stress), such that rupture of the membrane 620 is caused by the mechanical stress that is induced in the membrane 620 by virtue of the localized heating of a small portion of the membrane, as discussed above. In addition, in the embodiment of FIG. 6B, depending on the CTE (coefficient of thermal expansion) of the material used to form the electrode structure 640, when current flows through the electrode structure 640, an expansion force (denoted by arrow E in FIG. 6B) can also be imparted to the membrane 620 by virtue of heating and thermal expansion of the electrode structure 640. The expansion force E exerted by the electrode structure 640 on the membrane 620, coupled with the mechanical stress caused by the localized heating of the membrane 620, can assist in causing a rupture in the locally heated portion 650 of the membrane 620.

In another embodiment of the invention, low-power release is further achieved by forming one or more thin film layers (e.g., the silicon nitride layers 622, 624) of the membrane 620 in a state of internal tensile stress, which stresses the membrane 620 close to the elastic limit. In other words, the internal stress can be formed to a level that is close to, but does not exceed, a stress level which would cause spontaneous cracking and rupture of the membrane 620. By way of specific example, as shown in FIG. 6B, the membrane 620 can be formed with a tensile stress emanating from a central region of the membrane 620 (as indicated by the arrow T). In this embodiment, the tensile stress T of the membrane 620, the thermal expansion force E of the electrode structure 640, and the mechanical stress in the locally heated region 650 of the membrane, collectively provide a force that is sufficient to cause a rupture in at least the locally heated region 650 of the membrane 620. The apex 642A/644A of the V-shaped electrode 642/644 can be located near the center of the membrane 620, where maximum tensile pre-stress is present. Alternatively, the apex 642A/644A of the V-shaped electrode 642/644 can be located closer to the edge of the cavity 640 to increase the size of the opening. Indeed, when the membrane 620 is formed in a pre-stressed tensile state, once rupture occurs in the locally heated region 650, the tensile stress of the membrane 620 can cause portions of the membrane 620 to peel back away from the ruptured region of the membrane 620.

It is to be understood that the medical substance capsule devices illustrated in FIGS. 2, 3A/3B, 4, 5, and 6A/6B are presented herein for the purpose of providing example embodiments of medical substance capsule devices that can be used in conjunction with low-power control systems and actuation mechanism according to embodiments of the invention. Other medical substance capsule devices and structures (such as disclosed in the above-incorporated U.S. patent application Ser. Nos. 14/483,278 and 14/928,508) can be utilized, which implement low-power release mechanisms that are configured to break, melt, rupture, etc. a seal structure and/or lid structure in response to low-power control signals (e.g., voltage or current pulses) generated by, e.g., the control system 110 of FIG. 1. The control system 110 can be implemented using various circuit configurations and control methods, example embodiments of which will now be described in further detail with reference to FIGS. 7-14, for example.

For example, FIG. 7 is a block diagram of a control system which is configured to control the activation of a medical substance capsule device having a low-power release mechanism, according to an embodiment of the invention. In particular, FIG. 7 illustrates a control system 700 comprising control circuitry 710 which is configured to generate an activation signal S1 to activate a low-power release mechanism of a medical substance capsule 720. The control circuitry 710 is powered by a DC voltage (e.g., VDD) that is supplied by a pre-charged external power source 730. In alternative embodiments, the external power source 730 may comprise a bio-compatible thin-film battery or a capacitor-based power supply, which are charged prior to implantation, ingestion, etc., of the microchip medical substance delivery which comprises the control system 700.

The control circuitry 710 comprises a bandpass filter 711, an amplifier 712, an analog-to-digital (A/D) converter 713, a digital signal processor 714 and an actuator 715. The bandpass filter 711 has an input that is coupled to a signal receiving element 740. The signal receiving element 740 is configured to capture a wireless signal 742 which comprises an embedded activation code that is transmitted from a remote control source. More specifically, in one embodiment, the signal receiving element 740 comprises a planar antenna structure which is configured to receive an RF (radio frequency) carrier signal that is modulated by an activation code signal. For example, the planar antenna structure may comprise a planar loop antenna, folded dipole antenna, etc.

In another embodiment, the signal receiving element 740 comprises a MEMS transducer element which is configured to capture an ultrasonic carrier signal that is modulated by an activation code signal. For example, in one embodiment, the signal receiving element 740 may comprise a CMUT (capacitive micro machined ultrasonic transducer) device. The control circuitry 710 is configured to process and decode a received wireless signal 742 to determine if a proper activation code is included in the received wireless signal 742. In response to the control system 710 detecting the presence of a proper activation code in the received wireless signal 742, the control system 710 generates the activation signal Si to activate a low-power release mechanism of the medical substance capsule 720.

More specifically, the bandpass filter 711 is configured to filter an analog wireless signal 742 received by the signal receiving element 740. The bandpass filter 711 is configured to allow analog signals within a target range of operating frequencies to pass through to the control circuitry 710 for processing. The amplifier 712 is configured to amplify a filtered analog signal output from the bandpass filter 711. The A/D converter 713 is configured to convert the amplified analog signal, which is output from the amplifier 712, into a digital signal (e.g., a sequence of discrete samples). The digital signal processor 714 is configured to process the digital signals, which are output from the A/D converter 713, to determine if a proper activation code signal is included in the received wireless signal.

If the digital signal processor 714 determines that a proper activation code is included in the received wireless signal, the digital signal processor 714 generates and outputs an actuator control signal S2 to the actuator 715. In response, the actuator 715 generates an activation signal S1 (e.g., single voltage pulse, voltage pulse stream, a single current pulse, or a current pulse stream) to activate the release mechanism of the medical substance capsule 720. Depending on the particular release mechanism implemented by the medical substance capsule 720, the actuator 715 is configured to generate a voltage or current activation signal to activate release structure of the medical substance capsule 720. Example embodiments of the actuator 715 will be described in further detail below with reference to FIGS. 8 and 9, for example.

In one embodiment of the invention, the digital signal processor 714 comprises a workload-optimized processor that is configured to perform real-time discrete demodulation operations (e.g., frequency or amplitude demodulation) to decode digital signals that are output from the A/D converter 713. The demodulation signal processing operations are performed by the digital signal processor 714 to extract an activation code signal from a frequency or amplitude modulated carrier wave signal (received wireless signal 742) that is captured by the signal receiving element 740, and digitized by the A/D converter 713. The digital signal processor 714 compares the extracted activation code signal with a pre-programmed activation code that is persistently stored a memory of the control system 710 (e.g., programmable ROM 170, FIG. 1). It is to be understood that any type of frequency or amplitude modulation/demodulation scheme can be implemented, which is suitable for the given application, to transmit and extract activation codes for controlling the activation of medical substance capsules.

To limit power usage of the control system 710, the digital signal processor 714 can be maintained in a sleep mode, wherein the digital signal processor 714 wakes up in response to a digital signal being output from the A/D converter to determine if a received signal comprises a proper activation code. In this regard, wireless signals which pass through the bandpass filter 711 and are digitized by the A/D converter 7134, may or may not be valid activation signals, depending on whether the wireless signals comprise a valid activation code. When an activation signal (e.g., carrier signal modulated with an activation code signal) is transmitted from a remote source, the activation signal can be transmitted over a given period of time with the activation code signal transmitted multiple times in sequence within that given period of time. The time period of transmission should be long enough to provide sufficient time for the wireless signal to propagate through the front-end circuitry (e.g., 711, 712, 713) and for the digital signal processor 714 to wake up and perform demodulation functions to determine if the received signal comprises a valid activation code.

For ease of illustration, FIG. 7 shows only one medical substance capsule 720. However, it is to be understood that the medical substance capsule 720 in FIG. 7 may be one of a plurality of electronically-addressable medical substance capsules within a dispensing array (e.g., dispensing array 120, FIG. 1). In this regard, for ease of illustration, FIG. 7 omits the selection circuitry (e.g., de-multiplexer circuitry 160, FIG. 1) that is controlled by the digital signal processor 714, for example, to select a given one of the electronically-addressable medical substance capsules within a dispensing array. In one embodiment of the invention, the selection circuitry (e.g., de-multiplexer circuitry) would be coupled to an output of the actuator 715 to direct the activation signal Si to the medical substance capsule that is selected by the selection circuitry. The selection circuitry may comprise any suitable combinatorial logic or decoding circuitry (which is controlled by select control signals generated by the digital signal processor 714, for example) to selectively apply the activation signal S1 to at least one selected medical substance capsule in an array of medical substance capsules.

Figure 8:
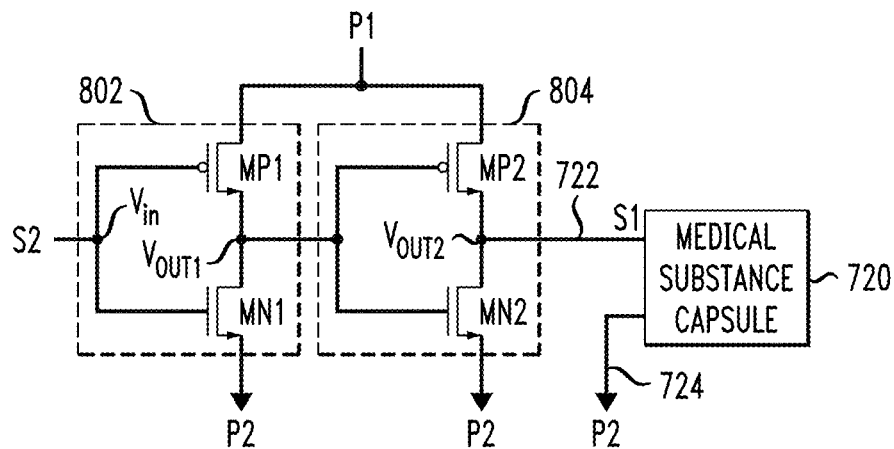
FIG. 8 is a schematic circuit diagram of an actuator which can be implemented as part of a control system to control the activation of a medical substance capsule device, according to an embodiment of the invention.

FIG. 8 is a schematic circuit diagram of an actuator which can be implemented as part of a control system to control the activation of a medical substance capsule device, according to an embodiment of the invention. More specifically, FIG. 8 illustrates an example embodiment of the actuator 715 of FIG. 7, which is configured to output a voltage activation signal. The actuator 800 comprises a cascading inverter pair, comprising a first CMOS inverter 802 and a second CMOS inverter 804. The first CMOS inverter 802 comprises a n-type FET (field effect transistor) MN1 and a p-type FET MP1, which are serially connected between a first power supply node P1 (e.g., VDD) and a second power supply node P2 (e.g., ground potential). The transistors MN1 and MP1 have gate terminals that are connected to each other and provide an input node $V_{IN}$ that receives an actuator control signal S2 from the digital signal processor 714 (FIG. 7). The second CMOS inverter 804 comprises a n-type FET MN2 and a p-type FET MP2, which are serially connected between the first and second power supply nodes P1 and P2. The transistors MN2 and MP2 have gate terminals which are commonly connected to each other and to an output node $V_{OUT1}$ of the first CMOS inverter 802. The second CMOS inverter 804 comprises an output node $V_{OUT2}$, which is coupled to a first electrode 722 of the medical substance capsule 720. A second electrode 724 of the medical substance capsule 720 is coupled to the second power supply node P2.

The actuator circuit 800 of FIG. 8 operates as follows. When a logic "1" is asserted at the input node $V_{IN}$, the output node $V_{OUT2}$ is connected to the first power supply node P1, which causes a power supply voltage VDD (generated by a battery or other regulated voltage source connected to P1) to be applied to the first electrode 722 of the medical substance capsule 720. The release mechanism of the medical substance capsule 720 is activated in response to a voltage VDD being applied to the first electrode 722 of the medical substance capsule 720. On the other hand, when a logic "0" is asserted at the input node $V_{IN}$, the output node $V_{OUT2}$ is connected to the second power supply node P2 (e.g., ground). In this state, since both the first and second electrodes 722 and 724 of the medical substance capsule 720 are connected to the same potential (e.g., ground), the medical substance capsule 720 is in a "de-activated" state.

In this regard, the actuator circuit 800 of FIG. 8 provides a voltage activation source for activating a medical substance capsule. Depending on the actuator control signal S2 applied to the input node $V_{IN}$ of the actuator circuit 800, the activation signal S1 (which is generated at the output node $V_{OUT2}$ of the actuator circuit 800 and applied to the first electrode 722) may comprise either a voltage pulse stream or a continuous DC voltage, which is applied for a sufficient amount of time to cause proper activation of the release mechanism of the medical substance capsule 720.

Figure 9:
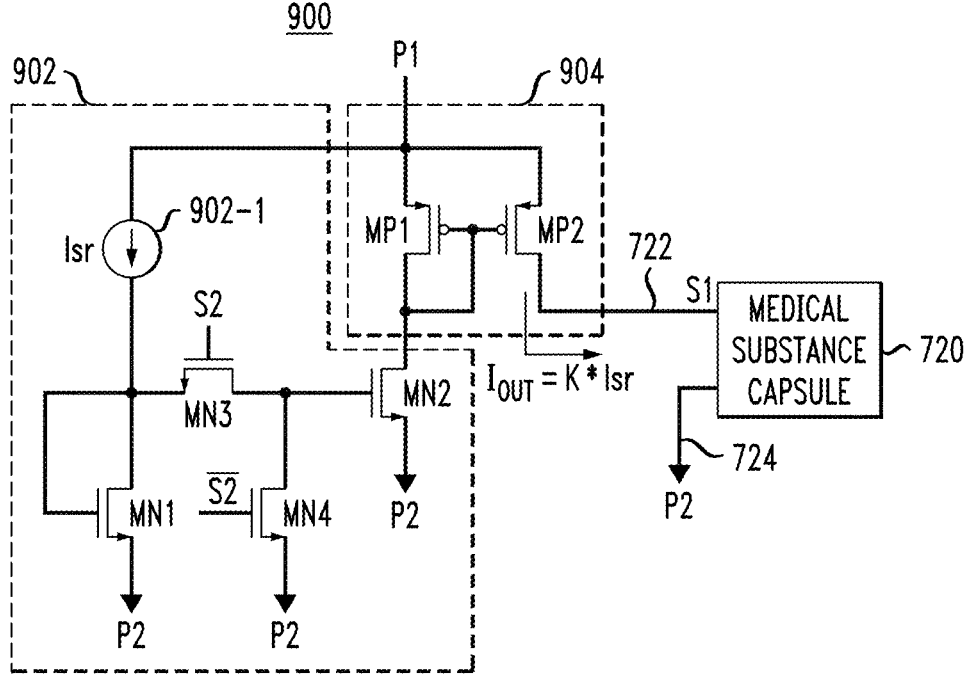
FIG. 9 is a schematic circuit diagram of an actuator which can be implemented as part of a control system to control the activation of a medical substance capsule device, according to another embodiment of the invention.

FIG. 9 is a schematic circuit diagram of an actuator which can be implemented as part of a control system to control the activation of a medical substance capsule device, according to another embodiment of the invention. More specifically, FIG. 9 illustrates an example embodiment of the actuator 715 of FIG. 7, which is configured to output a current activation signal. The actuator 900 comprises a current mirror 902 and a current source 904. The current mirror 902 comprises a reference current source 902-1 (which generates a current Isr), current mirror transistors MN1 and MN2 (n-type FETs), and control transistors MN3 and MN4 (n-type FETs). The current source 904 comprises p-type FET transistors MP1 and MP2.

The actuator circuit 900 of FIG. 9 operates as follows. The reference current source 902-1 sets a drain current (Isr) in the transistor MN1, and the current (Isr) is mirrored into a drain of the transistor MN2. In this configuration, the current mirror 902 sets a drain current of Isr in the transistor MP1 of the current source 904. The current source 904 outputs a current $I_{OUT}$=K*Isr, which is a multiple K of the mirrored current Isr. The multiple K is essentially equal to the ratio of:

$$\frac{W2/L2}{W1/L1},$$

wherein W2 and L2 denote the channel width and length of the transistor MP2, and wherein W1 and L1 denote the channel width and length of the transistor MP1 of the current source 904.

As further shown in FIG. 9, the control transistors MN3 and MN4 have gate terminals that receive complementary actuator control signals S2 and $\overline{S2}$, respectively, to control the activation and deactivation of the actuator circuit 900. The actuator circuit 900 is activated when S2 is asserted at a logic "1" level, and deactivated when S2 is asserted at a logic "0" level. In particular, when S2 is logic "1", the control transistor MN3 is in an "ON" state, and the control transistor MN4 is in an "OFF" state, which enables operation of the current mirror circuit 902 and the current source 904, wherein the current source 904 outputs the current $I_{OUT}$=K*Isr to the first electrode 722 of the medical substance capsule 720. On the other hand, when S2 is logic "0", the control transistor MN3 is in an "OFF" state, and the control transistor MN4 is in an "ON" state, which results in deactivation of the transistor MN2. With MN2 deactivated, the current source 904 does not operate, and no current is applied to the first electrode 722 of the medical substance capsule 720.

In this regard, the actuator circuit 900 of FIG. 9 provides a current activation source for activating a medical substance capsule. Depending on the complementary logic levels of the actuator control signal S2 applied to the control inputs (e.g., gate terminals of transistors MN3 and MN4) of the actuator circuit 900, the activation signal S1 (i.e., the current $I_{OUT}$=K*Isr that is applied to the first electrode 722) may comprise either a current pulse stream or a continuous DC current, which is applied for a sufficient amount of time to cause proper activation of the release mechanism of the medical substance capsule 720.

Figure 10:
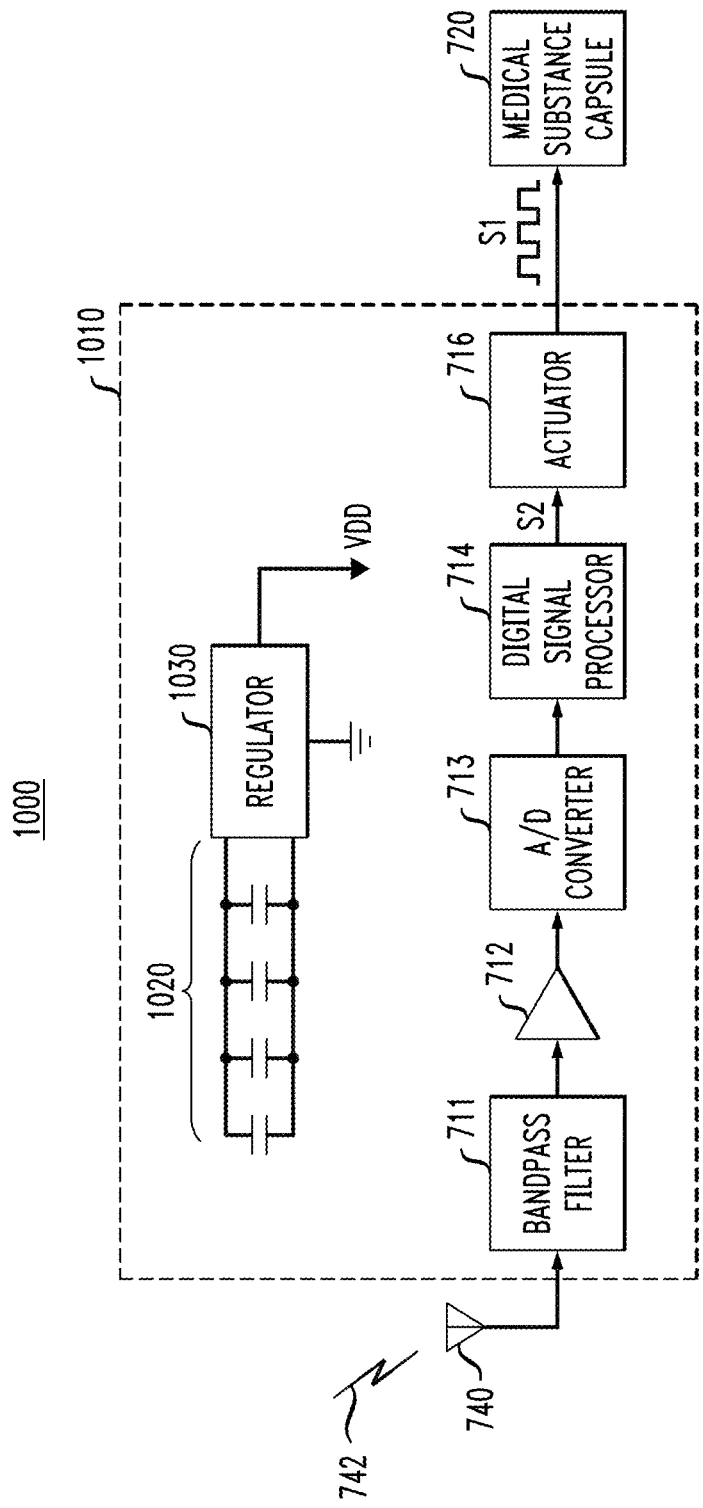
FIG. 10 is a block diagram of a control system which is configured to control the activation of a medical substance capsule device, according to another embodiment of the invention.

FIG. 10 is a block diagram of a control system which is configured to control the activation of a medical substance capsule device having a low-power release mechanism, according to another embodiment of the invention. In particular, FIG. 10 illustrates a control system 1000 comprising control circuitry 1010 which is similar to the control circuitry 710 of FIG. 7. However, instead of an external power source 730 as shown in FIG. 7, the control circuitry 1010 of FIG. 10 comprises an integrated on-chip capacitor power supply 1020, and a voltage regulator circuit 1030, which collectively operate to provide a DC power supply for various circuit components of the control circuitry 1010.

The on-chip capacitor power supply 1020 may be implemented using one of various types of on-chip capacitor structures such as MIM (metal-insulator-metal) capacitors, MOM (metal-oxide metal) capacitors, MOS (metal oxide semiconductor) capacitors, embedded DRAM capacitors, etc. The on-chip capacitor power supply 1020 is pre-charged prior to implantation, ingestion, etc., of the microchip medical substance delivery which comprises the control system 1000. The voltage regulator circuit 1030 is configured to regulate the voltage of the on-chip capacitor power supply 1020 and output a regulated supply voltage (e.g., VDD). The voltage regulator 1030 can be implemented using known circuit topologies and techniques, which are suitable for the given application. The operation and function of the various components 711, 712, 713, 714, 715 and 740 shown in FIG. 10 is the same as discussed above with reference to FIG. 7.

Figure 11:
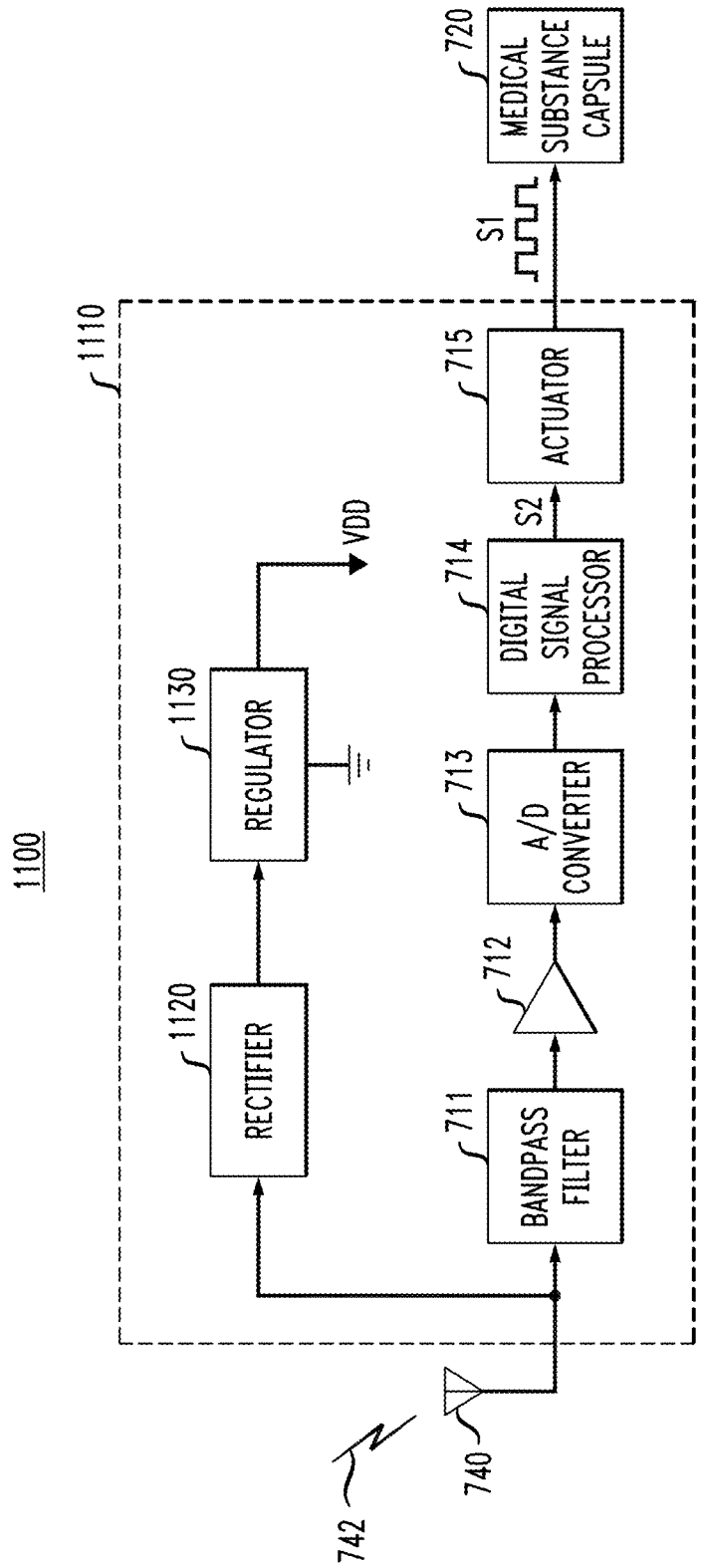
FIG. 11 is a block diagram of a control system which is configured to control the activation of a medical substance capsule device, according to another embodiment of the invention.

FIG. 11 is a block diagram of a control system which is configured to control the activation of a medical substance capsule device having a low-power release mechanism, according to another embodiment of the invention. In particular, FIG. 11 illustrates a control system 1100 comprising control circuitry 1110 which is similar to the control circuitry 710 of FIG. 7. However, instead of an external power source 730 as shown in FIG. 7, the control circuitry 1110 of FIG. 11 comprises a rectifier 1120 and a voltage regulator circuit 1130, which collectively operate to provide a DC power supply for various circuit components of the control circuitry 1110.

In particular, as shown in FIG. 11, an input of the rectifier circuit 1120 is connected to the signal receiving element 740. The rectifier circuit 1120 is configured to convert an AC voltage (at the output of the signal receiving element 740) into an unregulated DC voltage using known rectification techniques and circuit topologies. The unregulated DC voltage that is generated can be stored using an on-chip or external capacitor. The voltage regulator circuit 1130 is configured to generate a regulated supply voltage (e.g., VDD) based on the unregulated DC voltage generated by the rectifier circuit 1120. The voltage regulator 1130 can be implemented using known circuit topologies and techniques, which are suitable for the given application.

As compared to using pre-charged batteries or pre-charged capacitive-power supplies as in the embodiments discussed above in FIGS. 7 and 10, the embodiment of FIG. 11 utilizes the wireless signal 742 (e.g., ultrasound or RF signal) to generate a power supply voltage VDD to power-up the control circuitry 1110. In operation, an unmodulated carrier signal (or modulated carrier signal) can be transmitted for a certain period of time which is sufficient for the rectifier circuit 1120 and voltage regulator 1130 to generate a target power supply voltage level VDD. Once VDD reaches the target supply voltage level, the control circuitry 1110 then operates to process and decode a received wireless signal 742 to determine if a proper activation code is included in the received wireless signal 742, and generate an activation signal Si to activate a low-power release mechanism of the medical substance capsule 720 if a proper activation code is determined to be included in the received wireless signal 742. The operation and function of the various components 711, 712, 713, 714, 715 and 740 shown in FIG. 11 is the same as discussed above with reference to FIG. 7.

Figure 12:
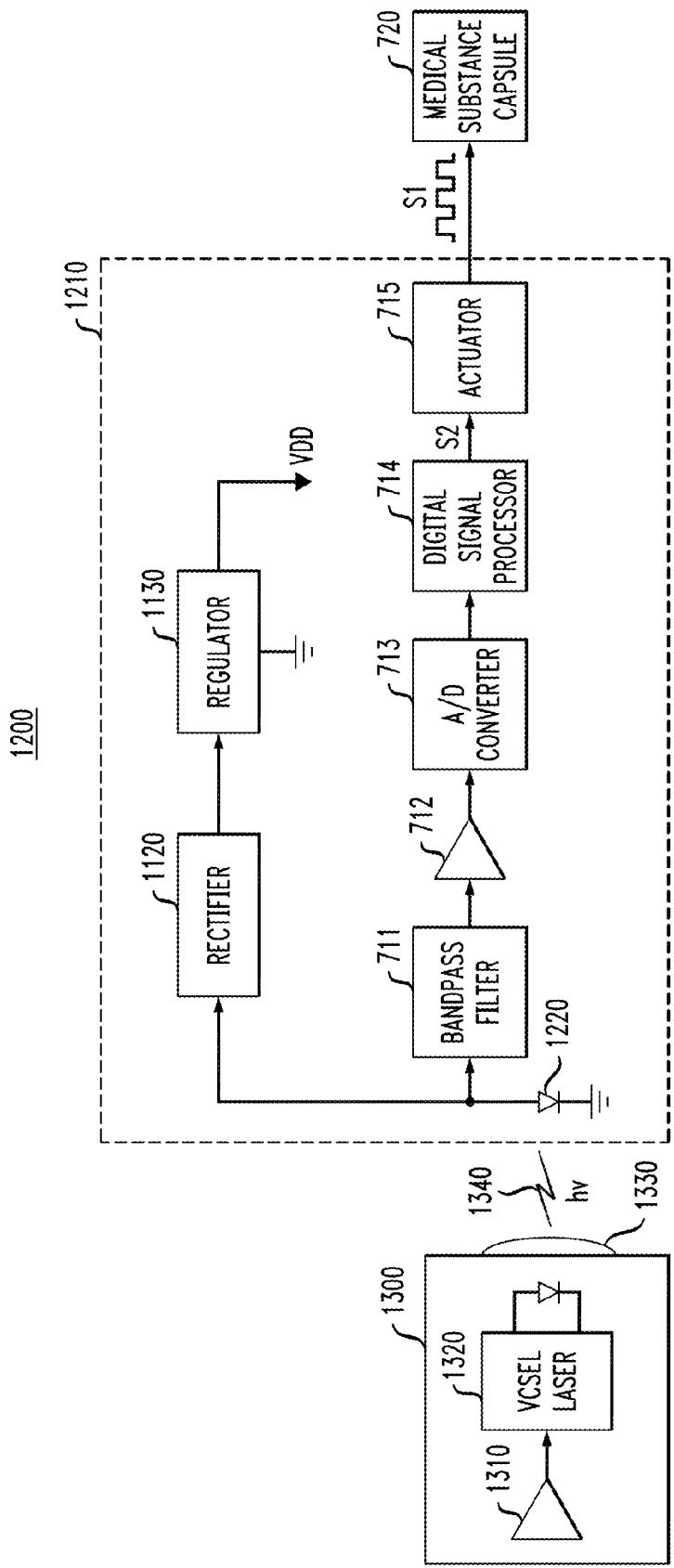
FIG. 12 is a block diagram of a control system which is configured to control the activation of a medical substance capsule device, according to another embodiment of the invention.

FIG. 12 is a block diagram of a control system which is configured to control the activation of a medical substance capsule device having a low-power release mechanism, according to another embodiment of the invention. In particular, FIG. 12 illustrates a control system 1200 comprising control circuitry 1210 which is configured to receive and process optical signals that are transmitted from an optical transmission system 1300, for purposes of generating DC power supply voltage and activating medical substance capsules. As shown in FIG. 12, the control circuitry 1210 is similar to the control circuitry 1110 of FIG. 11 in that the control system 1210 comprises various system components 711, 712, 713, 714, 714, 715, 1120, and 1130 which implement respective functions as discussed above.

In addition to these system components, the control circuitry 1210 comprises an optical receiver 1220 which is configured to receive optical signals transmitted from the optical transmission system 1300. In one embodiment of the invention, as discussed in further detail below with reference to FIGS. 13A and 13B, the optical receiver 1220 comprises plurality of photodiodes that are configured to operate in a photovoltaic mode without an external bias, to convert optical signals which are transmitted from the optical transmission system 1300 into electrical signals that are used to generate a DC power supply voltage and processed by the control circuitry 1210 to activate the medical substance capsule 720.

As further shown in FIG. 12, the optical transmission system 1300 comprises optical driver circuitry 1310, a laser-emitting device 1320, and an integrated lens 1330. The optical transmission system 1300 is configured to generate and transmit an optical signal 1340 (hv) which comprises an embedded activation code that is detected by the control circuitry 1210 to activate a release mechanism of the medical substance capsule 720. In one embodiment, the optical transmission system 1300 comprises a laser optical system, wherein the laser-emitting device 1320 comprises one or more laser diodes. More specifically, in one embodiment of the invention, the laser optical system comprises a vertical-cavity surface-emitting laser (VCSEL) system, wherein the laser-emitting device 1320 comprises a high-power VCSEL semiconductor laser diode that emits an optical laser beam perpendicular from a surface thereof.

The optical driver circuitry 1310 is configured to control modulation of the laser emitting device 1320 and cause the laser emitting device 1320 to generate and output a pulsed optical laser signal having the embedded activation code, using one of various optical modulation schemes known in the art. In one embodiment, the optical driver circuitry 1310 comprises circuitry that is configured to drive a VCSEL semiconductor laser diode. The driver circuitry 1310 is configured to modulate the emitted power of the laser-emitting device 1320, and emit a sequence of logic ones and zeros corresponding to pulses of high or low power, respectively. For example, the optical transmission system 1300 can be configured to output an optical signal 1340 (10 with two different intensities E0 and E1, wherein the intensity E0 represents a logic "0", and the intensity E1 represents a logic "1". In one embodiment of the invention, an activation code can be represented by transmitting an optical signal with a predefined sequence of logic 1s and 0s. In another embodiment, an activation code can be optically transmitted using an amplitude modulation scheme that implements more than two distinct intensities. Moreover, an optical signal can be modulated with an activation code by varying the duty cycle of the optically transmitted signal. Other suitable modulation schemes can be implemented to embed an activation code within an optical signal 1340 transmitted from the optical transmission system 1300 to the control system 1200.

In one embodiment, the integrated lens 1330 comprises a micro lens that is formed as part of the laser-emitting device 1320. The integrated lens 1330 is configured to collimate or otherwise focus the optical signals 1340 emitted from the laser-emitting device 1320 toward the microchip medical substance delivery device which comprises the control system 1200 of FIG. 12. The optical transmission system 1300 with the integrated lens 1330 may be used in circumstances where the microchip medical substance delivery device which comprises the control system 1200 is positioned within (or on) an individual such that the optical signals 1340 emitted from the optical transmission system 1300 can reach the optical receiver 1220 of the control system 1200. However, in circumstances where the microchip medical substance delivery device which comprises the control system 1200 is implanted deep within the body of an individual, for example, the optical transmission system 1300 may be utilized in conjunction with, or otherwise incorporated as part of, an endoscope device that is inserted into the body of the individual to reach the implanted microchip medical substance delivery device. In this embodiment, the optical signals generated by the laser-emitting device 1320 are transmitted to the implanted microchip medical substance delivery device using optical fibers of the endoscope device.

As noted above, the embodiment of FIG. 12 utilizes the optical signal 1340 (transmitted from the optical transmission system 1300) to generate a power supply voltage VDD to power-up the control circuitry 1210. In operation, an unmodulated optical signal (or a modulated optical signal) can be transmitted for a certain period of time which is sufficient for the optical receiver 1220, rectifier 1120, and voltage regulator 1130 to generate a target power supply voltage level VDD. Once VDD reaches the target supply voltage level, the control circuitry 1210 operates to process and decode a received optical signal 1340 to determine if a proper activation code is included in the received optical signal 1340, and generate an activation signal Si to activate a low-power release mechanism of the medical substance capsule 720 if a proper activation code is determined to be included in the receive optical signal 1340. The operation and function of the various components 711, 712, 713, 714, 715, 1120, and 1130 as shown in FIG. 12 is the same as discussed above with reference to FIGS. 7 and 11, for example.

Figure 13A:
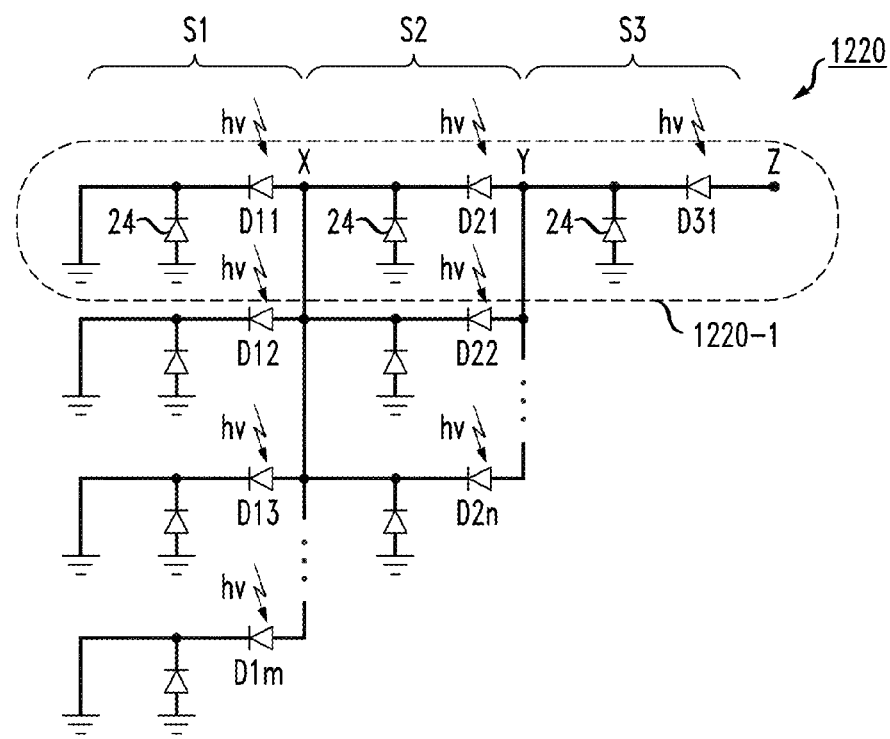
FIGS. 13A and 13B schematically illustrate an embodiment of an optical receiver which can be implemented in the control system of FIG. 12, according to an embodiment of the invention.
Figure 13B:
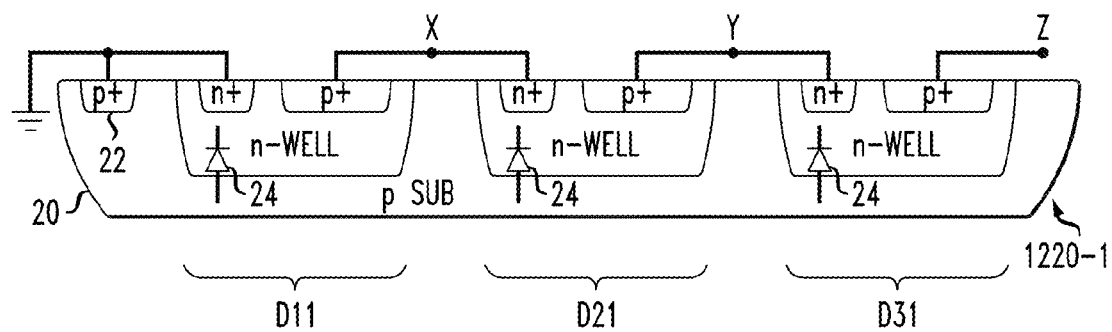

As further noted above, the optical receiver 1220 can be implemented using plurality of photodiodes that are configured to operate in a photovoltaic mode without an external bias. For example, FIGS. 13A and 13B schematically illustrate an embodiment of the optical receiver 1220 which can be implemented in the control system 1200 of FIG. 12, according to an embodiment of the invention. In particular, FIG. 13A is a schematic diagram of the optical receiver 1220 which comprises a stack of photodiodes according to an embodiment of the invention. The optical receiver 1220 comprises a plurality of photodiode stages S1, S2 and S3 that are serially connected between an output node Z and ground. The photodiode stage S3 comprises photodiode D31 connected between the output node Z of the optical receiver 1220 and an output node Y of the photodiode stage S2. The photodiode stage S2 comprises a plurality of photodiodes D21, D22, . . . , D2n, which are connected in parallel between the node Y and an output node X of the photodiode stage S1. The photodiode stage Si comprises a plurality of photodiodes D11, D12, . . . , D1m, which are connected in parallel between the node X and a ground terminal.

FIG. 13B schematically illustrates a semiconductor substrate comprising the photodiode stack of FIG. 13A. In particular, FIG. 13B is a schematic cross-sectional view of a semiconductor substrate 20 comprising a portion 1220-1 of the photodiode stack of FIG. 13A. As shown in FIG. 13B, the photodiodes D11, D21, and D31 of FIG. 13A are serially connected between the output node Z and ground. In one embodiment of the invention, as shown in FIG. 13B, the substrate 20 comprises a p-doped substrate which is connected to ground terminal via a p+ doped region 22. The grounding of the p-doped substrate 20 effectively provides a reversed biased diode junction 24 between the p-doped substrate 20 and each n-Well of the respective photodiodes D11, D21, and D31, as shown in FIGS. 13A and 13B, which provides isolation and prevents leakage of current.

The on-chip integrated photodiode stack configuration of the optical receiver 1220, which comprises a plurality of series and parallel-connected photodiodes, is configured to generate a large on-chip voltage. In silicon, a single photodiode operating in a photovoltaic mode can generate a voltage in a range of about 0.3V to about 0.4V. In the stacked photodiode configuration of FIGS. 13A and 13B, an output voltage of about 1.2V to 1.3V can be generated at the output node Z with current flowing through a load resistance connected to node Z. Indeed, with the stacked photodiode configuration, extra current flows in the parallel diodes connected to ground, that is, connected to nodes X and Y. The additional photodiode stages S2 and S3 enable larger currents to flow out of node Z.

Referring back to FIG. 12, the optical receiver 1220 is configured to transform the received optical signal 1340 (hv) into an electrical AC signal having substantially the same pulse sequence (logic ones and zeros) and duty cycle as the optical signal 1340, e.g., the electrical AC signal generated at the output of the optical receiver 1120 comprises a representation of the embedded activation code within the optical signal. For example, in one embodiment of the invention, the optical receiver 1220 outputs a series of voltage pulses (in response to an incident optical signal) with a pulse magnitude of about 1.2V to 1.3V and a period and duty cycle equal to the period and duty cycle of the optical pulses of the transmitted optical signal. The rectifier 1120 converts the electrical AC output of the optical receiver 1220 into an unregulated DC voltage, and the voltage regulator 1130 outputs a regulated DC voltage VDD based on the output of the rectifier 1120. For example, in one embodiment of the invention, the voltage regulator 1130 generates a regulated DC voltage of VDD=1V from the AC signal (voltage pulses with magnitude of about 1.2V to 1.3V) output from the optical receiver 1220. In one embodiment of the invention, the voltage regulator 1130 can be implemented using any voltage regulation framework comprising, e.g., a low-pass filter and analog regulator circuitry, which is suitable for the given application.

Figure 14:
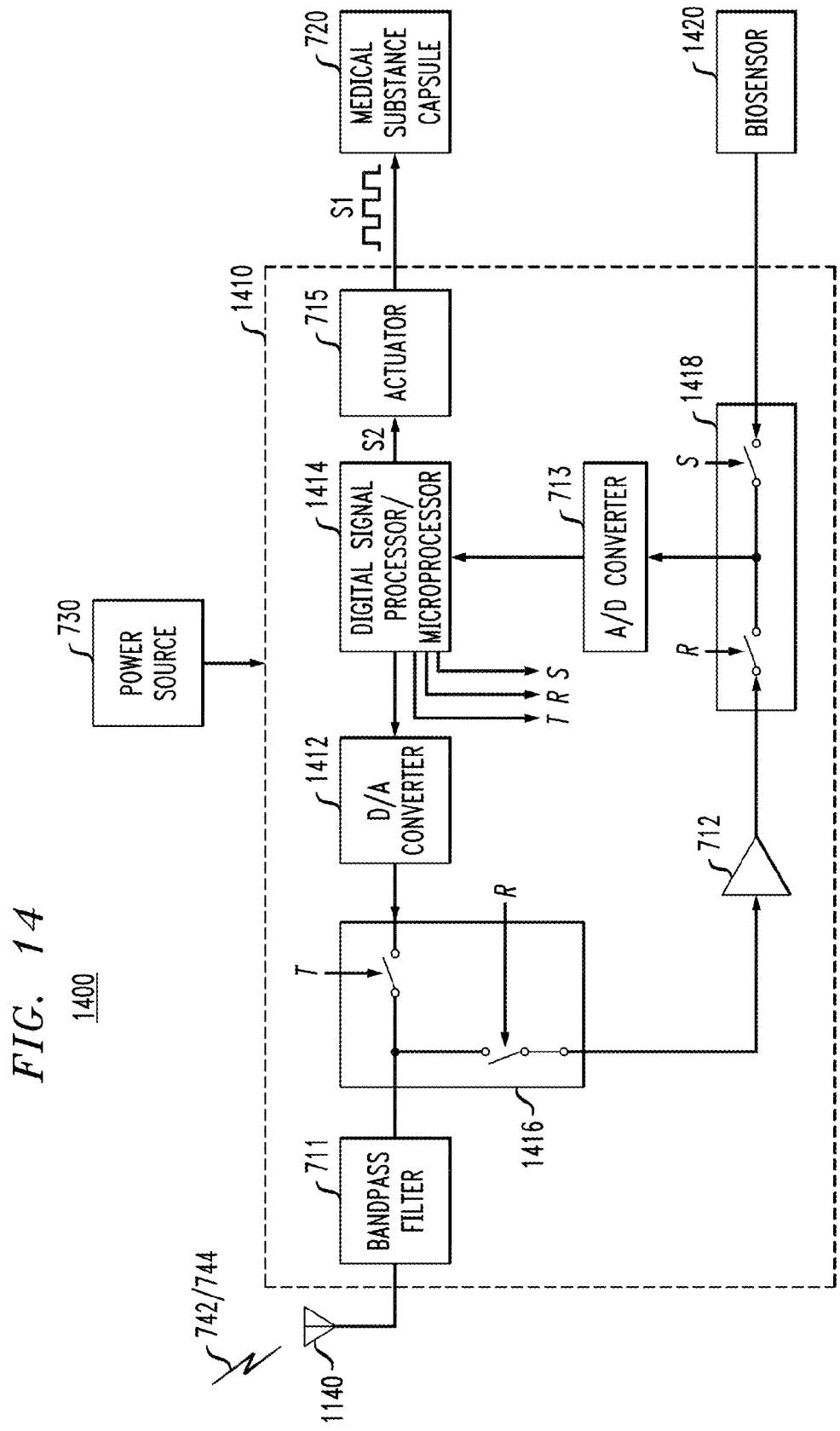
FIG. 14 is a block diagram of a control system which is configured to control the activation of a medical substance capsule device, according to another embodiment of the invention.

FIG. 14 is a block diagram of a control system which is configured to control the activation of a medical substance capsule device having a low-power release mechanism, according to another embodiment of the invention. In particular, FIG. 14 illustrates a control system 1400 which is similar to the control system 700 of FIG. 7, but which implements one of more biosensor components for adaptive medical substance delivery, as well as control circuitry to read, process, and transmit sensor data that is generated by the one or more biosensors. In particular, the control system 1400 comprises control circuitry 1410 which comprise a bandpass filter 711, amplifier 712, A/D converter 713, actuator 715, and external power source 730, similar to the embodiments discussed above with reference to FIGS. 7, 8 and 9, for example. However, the control circuitry 1410 of FIG. 14, further comprises a D/A (digital-to-analog) converter 1412, a digital signal processor/microcontroller (DSP/uC) 1414, a first switch 1416, and a second switch 1418. In addition, the control system 1400 comprises one or more biosensors 1420 and a signal receiving/transmitting element 1140. The one or more biosensors 1420 can be fabricated as part of the same microchip on which the control system 1400 is fabricated.

The control system 1400 of FIG. 14 is configured to operate in one of a plurality of operating modes, including, for example, a receive mode (R), a transmission mode (T), or a biosensor read mode (S). The operating mode of the control system 1400 is controlled by the DSP/uC 1414, which generates one of a plurality of control signals T (transmit), R (receive) or S (sensor read), depending on the operating mode of the control system 1400. As shown in FIG. 14, the first switch 1416 is controlled by the control signals T and R, and the second switch 1418 is controlled by the control signals R and S. In one embodiment, the first and second switches 1416 and 1418 can be implemented using any suitable switching circuitry, e.g., FET transistors that are activated and deactivated depending on the logic level (e.g., logic "1" or logic "0") of the control signals T, R, S applied to gate terminals thereof, etc.

In a receive mode (R), the control circuitry 1410 is configured to receive, process, and decode a received wireless signal 742 (which is received by the signal receiving/transmitting element 1740) to determine if a proper activation code is included in the received wireless signal 742, and generate an activation signal Si to activate a low-power release mechanism of the medical substance capsule 720, using methods as discussed above. Indeed, in the receive mode (R), the control signal R causes the first switch 1416 to connect the output of the filter 711 to the input of the amplifier 712, and causes the second switch 1418 to connect the output of the amplifier 712 to the A/D converter 713.

In the biosensor read mode (S), the control circuitry 1410 is configured to read and process sensor information obtained from one or more of the biosensors 1420. Indeed, in the biosensor read mode (S), the control signal S causes the second switch 1418 to connect the electrical signal output of the biosensor 1420 to the A/D converter 713. In the biosensor read mode (S), the control circuitry 1410 acquires analog sensor information from the biosensor 1420, which is digitized by the A/D converter 713, and processed by the DSP/uC 1414. Depending on the target medical condition being monitored, the biosensor 1420 can be configured using known techniques to measure biomarkers of cancer, infection, and other types disease or other physiological conditions within an individual's body, or otherwise monitor and detect levels of hormones, enzymes, and other types of metabolism-related molecules in the blood of an individual, etc., and generate electrical signals that are indicative of the measured, monitored and/or detected conditions.

In one embodiment, the DSP/uC 1414 is configured to automatically access and process sensor information from the biosensor 1420, and thereby automatically control activation of medical substance capsules based on the processed sensor information. In particular, the DSP/uC 1414 can be configured to access and process the sensor information based on program instructions that are locally stored in a ROM device and executed by the DSP/uC 1414, and determine if and when to activate a medical substance capsule and release a medical substance based on the results of processing the obtained biosensor information. In this regard, the embodiment of FIG. 14 may be utilized in applications wherein the measuring/monitoring is performed on a regular basis, and wherein the continuous or periodic delivery of a medial substance is automatically performed by operation of the control circuitry 1410 based on the sensor data obtained from the biosensor 1420.

In another embodiment, the DSP/uC 1414 can configure the control circuitry 1410 to operate in a transmit mode (T) to transmit the obtained biosensor information to a remote source for remote logging and processing. In particular, in the transmit mode (T), the DSP/uC 1414 outputs a control signal T which causes the first switch 1416 to connect the output of the D/A converter 1412 to the filter 711. Furthermore, in the transmit mode (T), the DSP/uC 1414 performs digital modulation functions to encode the digitized biosensor information using any suitable digital modulation scheme (e.g., ASK (amplitude-shift keying), PSK (phase-shift keying), FSK (frequency-shift keying), etc.). With this encoding scheme, modulation is performed by the DSP/uC 1414 in the digital domain, and the resulting encoded digital waveform is output to the D/A converter 1412. The D/A converter 1412 is configured to convert the encoded digital waveform to an analog signal, wherein the resulting analog signal 744 is transmitted to the remote source via the signal receiving/transmitting element 1140.

In the embodiment of FIG. 14, although one signal receiving/transmitting element 1140 is shown, the control system can be implemented with two separate antennas or transducers, one for transmit and one for receive. In addition, the bandpass filter 711 can be implemented in conjunction with additional filter circuitry (e.g., low pass filter circuitry) to provide proper impedance matching between the active components of the D/A converter 1412 and the impedance of the signal receiving/transmitting element 1140, and to reject harmonics and spurious emissions, etc., when operating in the transmit mode (T).

Figure 15:
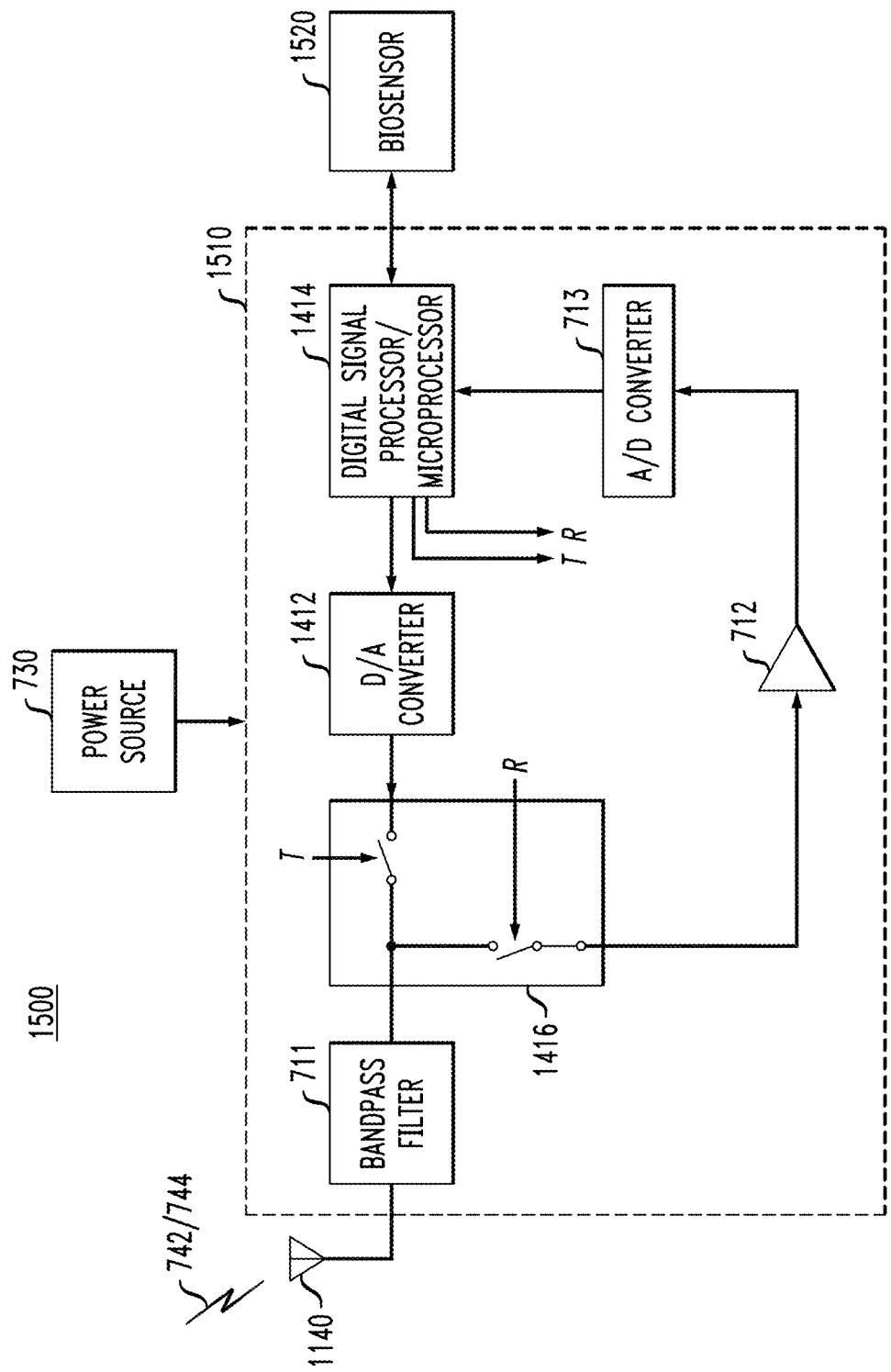
FIG. 15 is a block diagram of a control system which is configured to control a biosensor, according to an embodiment of the invention.

FIG. 15 is a block diagram of a control system which is configured to control a biosensor, according to an embodiment of the invention. In particular, FIG. 15 illustrates a control system 1500 which is similar to the control system 1400 of FIG. 14, but which comprises control circuitry 1510 that is configured to read, process, and transmit (to a remote source) digital sensor data that is generated by at least one biosensor 1520. In particular, the control circuitry 1510 comprises a bandpass filter 711, switch 1416, amplifier 712, A/D converter 713, DSP/uC 1414, and D/A converter 1412, which have the same or similar functions as discussed above. However, in the embodiment of FIG. 15, the biosensor 1520 is coupled to the DSP/uC 1414 to receive sensor data read commands from the DSP/uC 1414. In response to a sensor data read command, the biosensor 1520 outputs digital sensor data to the DSP/uC 1414, which is encoded and transmitted to a remote source. The biosensor 1520 can be fabricated as part of the same microchip on which the control system 1500 is fabricated. In embodiments where the biosensor 1520 generates analog sensor data, the control circuitry 1410 of FIG. 14 can be implemented wherein the output of the biosensor 1420 is routed to the input of the A/D converter 713 via the second switch 1418.

The control system 1500 of FIG. 15 is configured to operate in one of a plurality of operating modes, including, for example, a receive mode (R) and a transmission mode (T). The operating mode of the control system 1500 is controlled by the DSP/uC 1414, which generates one of a plurality of control signals T (transmit) or R (receive), depending on the operating mode of the control system 1500. In a receive mode (R), the DSP/uC 1414 outputs a control signal R, which causes the switch 1416 to connect the output of the bandpass filter 711 to the input of the amplifier 712, and place the control circuitry 1510 in a "wait state" for a "sensor data acquisition" command that may be transmitted from a remote source.

In the receive mode (R), when a wireless signal 742 is received via the signal receiving/transmitting element 1140, the wireless signal 742 is filtered by the bandpass filter 711, amplified by the amplifier 712, and digitized by the A/D converter 713. The digitized signal is processed by the DSP/uC 1414 to determine if a valid sensor data acquisition command is included in the received wireless signal 742 (e.g., the digitized signal is demodulated to extract a baseband sensor data acquisition signal (if present), and the extracted baseband sensor data acquisition signal is compared to a predefined sensor data acquisition command, etc.). If the DSP/uC 1414 determines that a valid sensor data acquisition command is included in the received wireless signal 742, the DSP/uC 1414 generates and outputs a sensor read command to the biosensor 1520 to acquire sensor data from the biosensor 1520.

Furthermore, the DSP/uC 1414 configures the control circuitry 1510 to operate in a transmit mode (T) to transmit the obtained biosensor information to a remote source for logging and processing. In particular, in the transmit mode (T), the DSP/uC 1414 outputs a control signal T which causes the switch 1416 to connect the output of the D/A converter 1412 to the filter 711. Furthermore, in the transmit mode (T), the DSP/uC 1414 performs digital modulation functions to encode the digital sensor data (received from the biosensor 1520) using any suitable digital modulation scheme (e.g., ASK, PSK, FSK, etc.). With this encoding scheme, modulation is performed by the DSP/uC 1414 in the digital domain, and the resulting encoded digital waveform is output to the D/A converter 1412. The D/A converter 1412 is configured to convert the encoded digital waveform to an analog signal, wherein the resulting analog signal 744 is transmitted (via the signal receiving/transmitting element 1140) to the remote source which requested the sensor data.

The embodiment of FIG. 15 can be utilized for applications in which a biosensor is deployed for on-demand measurement and acquisition of sensor data that is indicative of biomarkers of cancer, infection, and other types of disease or physiological conditions within an individual's body. For example, assume an individual had knee replacement or hip replacement surgery. One or more microchips having the control system 1500 of FIG. 15 can be implanted within the individual in proximity to the replaced knee or hip to monitor/detect for the possible development of infection over time. In this circumstance, a doctor can periodically (e.g., monthly, semi-annually, etc.) obtain sensor data from the one or more implanted biosensors to determine if any infection has begun to develop within the individual in proximity to the replaced knee or hip. If infection is detected, the person can take antibiotics orally, for example, without the use of an implanted medical substance delivery system.

Although embodiments have been described herein with reference to the accompanying drawings for purposes of illustration, it is to be understood that the present invention is not limited to those precise embodiments, and that various other changes and modifications may be affected herein by one skilled in the art without departing from the scope of the invention.

We claim:

1. A microchip medical substance delivery device, comprising:
    a control system; and
    a medical substance capsule comprising a substrate comprising a plurality of cavities etched in the substrate, wherein each cavity provides a reservoir which contains a medical substance, and a release structure configured to release the medical substance from within the reservoir in response to an activation signal generated by the control system;
    wherein the control system comprises:
        a wireless signal receiving element configured to capture a wireless signal;
        a processor configured to detect a presence of an activation code embedded within the captured wireless signal, and generate an actuator control signal in response to the detection of the activation code within the captured wireless signal;
        an actuator circuit configured to generate the activation signal in response to the actuator control signal generated by the processor, and apply the activation signal to the medical substance capsule to activate the release structure and release the medical substance from within the reservoir of the medical substance capsule; and
        a power supply source configured to provide DC (direct current) power supply voltage to operate components of the control system.

2. The device of claim 1, wherein the actuator circuit is configured to generate an electrical pulse stream as the activation signal.

3. The device of claim 2, wherein the electrical pulse stream comprises a voltage pulse stream.

4. The device of claim 2, wherein the electrical pulse stream comprises a current pulse stream.

5. The device of claim 1, wherein the power supply source comprises:
    one or more pre-charged capacitors to store an unregulated voltage; and
    a voltage regulator configured to generate a regulated supply voltage based on the unregulated voltage stored by the one or more pre-charged capacitors.

6. The device of claim 1, wherein the captured wireless signal comprises an ultrasonic signal that is modulated to include the activation code.

7. The device of claim 1, wherein the captured wireless signal comprises an optical signal that is modulated to include the activation code.

8. The device of claim 7, wherein the power supply source comprises:
    a photodiode array configured convert the optical signal to an electrical signal;
    a rectifier circuit configured to generate an unregulated voltage by rectifying the electrical signal output from the photodiode array; and
    a voltage regulator configured to generate a regulated supply voltage based on the unregulated voltage generated by the rectifier circuit.

9. The device of claim 1, wherein the device comprises an implantable microchip medical substance delivery device.

10. The device of claim 1, wherein the device comprises an ingestible microchip medical substance delivery device.

11. A microchip medical substance delivery device, comprising:
    a control system; and
    a medical substance capsule comprising a medical substance contained in a reservoir, and a release structure configured to release the medical substance from within the reservoir in response to an activation signal generated by the control system;
    wherein the control system comprises:
        a wireless signal receiving element configured to capture a wireless signal;
        a processor configured to detect a presence of an activation code embedded within the captured wireless signal, and generate an actuator control signal in response to the detection of the activation code within the captured wireless signal;
        an actuator circuit configured to generate the activation signal in response to the actuator control signal generated by the processor;
        a power supply source configured to provide DC (direct current) power supply voltage to operate components of the control system; and
        an A/D (analog-to-digital) converter configured to convert the captured wireless signal to a digitized signal, wherein the processor is configured to process the digitized signal to detect the presence of the activation code embedded within the captured wireless signal.

12. A microchip medical substance delivery device, comprising:
    a control system; and
    a medical substance capsule comprising a medical substance contained in a reservoir, and a release structure configured to release the medical substance from within the reservoir in response to an activation signal generated by the control system;
    wherein the control system comprises:
        a wireless signal receiving element configured to capture a wireless signal;
        a processor configured to detect a presence of an activation code embedded within the captured wireless signal, and generate an actuator control signal in response to the detection of the activation code within the captured wireless signal;
        an actuator circuit configured to generate the activation signal in response to the actuator control signal generated by the processor; and
        a power supply source configured to provide DC (direct current) power supply voltage to operate components of the control system;
        wherein the processor comprises a digital signal processor that is configured to perform discrete demodulation functions to demodulate the captured wireless signal and extract a modulating signal representative of the activation code.

13. A microchip medical substance delivery device, comprising:
    a control system; and a medical substance capsule comprising a medical substance contained in a reservoir, and a release structure configured to release the medical substance from within the reservoir in response to an activation signal generated by the control system;

wherein the control system comprises:
a wireless signal receiving element configured to capture a wireless signal;
a processor configured to detect a presence of an activation code embedded within the captured wireless signal, and generate an actuator control signal in response to the detection of the activation code within the captured wireless signal;
an actuator circuit configured to generate the activation signal in response to the actuator control signal generated by the processor; and
a power supply source configured to provide DC (direct current) power supply voltage to operate components of the control system;

wherein the power supply source comprises:
a rectifier circuit configured to generate an unregulated voltage by rectifying the captured wireless signal; and
a voltage regulator configured to generate a regulated supply voltage based on the unregulated voltage generated by the rectifier circuit.

14. A microchip medical substance delivery device, comprising:
a control system; and
a medical substance capsule comprising a medical substance contained in a reservoir, and a release structure configured to release the medical substance from within the reservoir in response to an activation signal generated by the control system;

wherein the control system comprises:
a wireless signal receiving element configured to capture a wireless signal;
a processor configured to detect a presence of an activation code embedded within the captured wireless signal, and generate an actuator control signal in response to the detection of the activation code within the captured wireless signal;
an actuator circuit configured to generate the activation signal in response to the actuator control signal generated by the processor; and
a power supply source configured to provide DC (direct current) power supply voltage to operate components of the control system;

wherein the control system is configurable to selectively operate in one of a plurality of operating modes including a receive mode, a sensor read mode, and a transmit mode;

wherein in the receive mode, the control system is configured to receive and process the captured wireless signal;
wherein in the sensor read mode, the control system is configured to read sensor information from a biosensor; and
wherein in the transmit mode, the control system is configured to transmit data to a remote source, wherein the data comprises the sensor information read from the biosensor.

15. The device of claim 14, wherein the biosensor is integrated with the device.

16. A method, comprising:
receiving a wireless signal by a microchip medical substance delivery device that is disposed within a body of an individual, wherein microchip medical substance delivery device comprises a control system, and a medical substance capsule, the medical substance capsule comprising a substrate comprising a plurality of cavities etched in the substrate, wherein each cavity provides a reservoir which contains a medical substance, and a release structure that is configured to release the medical substance from within the reservoir in response to an activation signal generated by the control system;
processing, by the control system, the received wireless signal to detect a presence of an activation code embedded within the captured wireless signal;
generating, by the control system, an actuator control signal in response to the detection of the activation code within the captured wireless signal;
generating, by the control system, the activation signal in response to the actuator control signal; and
applying the activation signal to the medical substance capsule to activate the release structure and release the medical substance from within the reservoir of the medical substance capsule.

17. The method of claim 16, wherein the wireless signal is received from a remote source outside of the body of the individual.

18. The method of claim 16, wherein generating the activation signal in response to the actuator control signal comprises generating one of a current pulse and a voltage pulse.

19. The method of claim 16, further comprising generating, by the control system, a DC power supply voltage by rectifying the received wireless signal, and utilizing the generated DC power supply voltage to generate the activation signal.

20. The method of claim 16, wherein the received wireless signal comprises one of an RF (radio frequency) signal, an ultrasonic signal, and an optical signal.

* * * * *